US009956042B2

(12) United States Patent
Simaan et al.

(10) Patent No.: US 9,956,042 B2
(45) Date of Patent: May 1, 2018

(54) SYSTEMS AND METHODS FOR ROBOT-ASSISTED TRANSURETHRAL EXPLORATION AND INTERVENTION

(71) Applicant: Vanderbilt University, Nashville, TN (US)

(72) Inventors: Nabil Simaan, Nashville, TN (US); Andrea Bajo, Fort Lauderdale, FL (US); Ryan B. Pickens, Nashville, TN (US); Stanley Duke Herrel, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 500 days.

(21) Appl. No.: 14/271,345

(22) Filed: May 6, 2014

(65) Prior Publication Data
US 2014/0316434 A1    Oct. 23, 2014

Related U.S. Application Data

(63) Continuation-in-part of application No. PCT/US2013/021167, filed on Jan. 11, 2013.
(Continued)

(51) Int. Cl.
*A61B 19/00* (2006.01)
*A61B 34/00* (2016.01)
(Continued)

(52) U.S. Cl.
CPC .......... *A61B 19/2203* (2013.01); *A61B 34/30* (2016.02); *A61B 34/74* (2016.02);
(Continued)

(58) Field of Classification Search
CPC .............. A61B 34/74; A61B 2034/302; A61B 2018/00517
(Continued)

(56) References Cited

U.S. PATENT DOCUMENTS

| 2,988,237 A | 6/1961 | Devol, Jr. |
| 3,580,099 A | 5/1971 | Mosher |

(Continued)

FOREIGN PATENT DOCUMENTS

| EP | 2335558 | 6/2011 |
| WO | 2005009482 | 2/2005 |

(Continued)

OTHER PUBLICATIONS

A. Bajo and N. Simaan, "Configuration and Joint Feedback for Enhanced Performance of Multi-Segment Continuum Robots," in IEEE International Conference on Robotics and Automation, 2011, pp. 2905-2912.
(Continued)

*Primary Examiner* — Diane Yabut
*Assistant Examiner* — Martin T Ton
(74) *Attorney, Agent, or Firm* — Michael Best & Friedrich LLP

(57) ABSTRACT

Systems and methods are described for using a robotic system to perform procedures within a cavity using a virtual fixture. The robotic system includes a rigid central stem including an access channel positioned longitudinally along the rigid central stem and a dexterous arm at least partially positioned within the access channel of the central stem. The dexterous arm includes a plurality of individually adjustable segments. A control system receives a positioning command from a manipulator control indicative of a desired movement of a distal end of the dexterous arm. A virtual fixture is defined that is representative of the access channel of the rigid central stem. The position of the dexterous arm is adjusted such that the distal end of the dexterous arm performs the desired movement while the portion of the dexterous arm that is positioned within the first access channel is not moved beyond the defined virtual fixture.

10 Claims, 11 Drawing Sheets

Related U.S. Application Data

(60) Provisional application No. 61/840,748, filed on Jun. 28, 2013, provisional application No. 61/586,458, filed on Jan. 13, 2012.

(51) Int. Cl.
  *A61B 18/24* (2006.01)
  *A61B 18/00* (2006.01)
  *A61B 34/30* (2016.01)

(52) U.S. Cl.
  CPC ..... *A61B 18/24* (2013.01); *A61B 2018/00517* (2013.01); *A61B 2018/00577* (2013.01); *A61B 2034/302* (2016.02)

(58) Field of Classification Search
  USPC .......................................................... 606/130
  See application file for complete search history.

(56) References Cited

U.S. PATENT DOCUMENTS

| | | | |
|---|---|---|---|
| 4,744,264 A | 5/1988 | Milenkovic | |
| 4,795,296 A | 1/1989 | Jau | |
| 4,802,461 A | 2/1989 | Cho | |
| 5,046,375 A | 9/1991 | Salisbury, Jr. et al. | |
| 5,231,989 A | 8/1993 | Middleman et al. | |
| 5,337,732 A | 8/1994 | Grundfest et al. | |
| 5,345,937 A | 9/1994 | Middleman et al. | |
| 5,386,741 A | 2/1995 | Rennex | |
| 5,397,323 A | 3/1995 | Taylor et al. | |
| 5,410,638 A | 4/1995 | Colgate et al. | |
| 5,480,406 A | 1/1996 | Nolan et al. | |
| 5,662,587 A | 9/1997 | Grundfest et al. | |
| 5,749,828 A | 5/1998 | Solomon et al. | |
| 6,113,593 A | 9/2000 | Tu et al. | |
| 6,197,017 B1 | 3/2001 | Brock et al. | |
| 6,309,346 B1 | 10/2001 | Farhadi | |
| 6,554,844 B2 | 4/2003 | Lee et al. | |
| 6,669,711 B1 | 12/2003 | Noda | |
| 6,676,684 B1 | 1/2004 | Morley et al. | |
| 6,692,485 B1 | 2/2004 | Brock et al. | |
| 6,817,974 B2 | 11/2004 | Cooper et al. | |
| 6,837,892 B2 | 1/2005 | Shoham | |
| 6,843,793 B2 | 1/2005 | Brock et al. | |
| 6,858,005 B2 | 2/2005 | Ohline et al. | |
| 6,860,878 B2 | 3/2005 | Brock | |
| 6,949,106 B2 | 9/2005 | Brock et al. | |
| 7,021,173 B2 | 4/2006 | Stoianovici et al. | |
| 7,099,745 B2 | 8/2006 | Ebert | |
| 7,214,230 B2 | 5/2007 | Brock et al. | |
| 7,235,089 B1 | 6/2007 | McGuckin, Jr. | |
| 7,316,681 B2 | 1/2008 | Madhani et al. | |
| 7,391,173 B2 | 6/2008 | Schena | |
| 7,682,319 B2 | 3/2010 | Martin et al. | |
| 7,699,835 B2 | 4/2010 | Lee et al. | |
| 7,787,681 B2 | 8/2010 | Zhang et al. | |
| 7,822,249 B2 | 10/2010 | Garty et al. | |
| 7,837,615 B2 | 11/2010 | Le et al. | |
| 7,854,738 B2 | 12/2010 | Lee et al. | |
| 7,887,549 B2 | 2/2011 | Wenderow et al. | |
| 7,959,557 B2 | 6/2011 | Weitzner et al. | |
| 8,025,635 B2 | 9/2011 | Eaton et al. | |
| 8,114,062 B2 | 2/2012 | Muni et al. | |
| 8,116,886 B2 | 2/2012 | Simaan et al. | |
| 8,172,828 B2 | 5/2012 | Chang et al. | |
| 8,088,101 B2 | 6/2012 | Chang et al. | |
| 8,303,576 B2 | 11/2012 | Brock | |
| 8,311,626 B2 | 11/2012 | Hlavka et al. | |
| 8,337,521 B2 | 12/2012 | Cooper et al. | |
| 8,343,141 B2 | 1/2013 | Madhani et al. | |
| 8,365,633 B2 | 2/2013 | Simaan et al. | |
| 8,372,019 B2 | 2/2013 | Goldenberg et al. | |
| 8,377,077 B2 | 2/2013 | Reis | |
| 8,409,234 B2 | 4/2013 | Stahler et al. | |
| 8,414,505 B1 | 4/2013 | Weitzner et al. | |
| 8,414,598 B2 | 4/2013 | Brock et al. | |
| 8,444,549 B2 | 5/2013 | Viola et al. | |
| 8,460,236 B2 | 6/2013 | Roelle et al. | |
| 8,480,618 B2 | 7/2013 | Wenderow et al. | |
| 8,486,053 B2 | 7/2013 | Niemeyer | |
| 8,498,691 B2 | 7/2013 | Moll et al. | |
| 8,504,201 B2 | 8/2013 | Moll et al. | |
| 8,545,551 B2 | 10/2013 | Loulmet | |
| 8,551,115 B2 | 10/2013 | Steger et al. | |
| 8,585,731 B2 | 11/2013 | Abbate et al. | |
| 8,864,757 B2 | 10/2014 | Klimovitch et al. | |
| 2002/0120252 A1 | 8/2002 | Brock et al. | |
| 2003/0120305 A1 | 6/2003 | Jud et al. | |
| 2004/0116906 A1 | 6/2004 | Lipow | |
| 2004/0176751 A1 | 9/2004 | Weitzner et al. | |
| 2005/0043718 A1 | 2/2005 | Madhani et al. | |
| 2005/0054900 A1 | 3/2005 | Mawn et al. | |
| 2005/0059960 A1 | 3/2005 | Simaan et al. | |
| 2005/0228440 A1 | 10/2005 | Brock et al. | |
| 2006/0036182 A1 | 2/2006 | Daniels et al. | |
| 2006/0047302 A1 | 3/2006 | Ortiz et al. | |
| 2006/0058861 A1 | 3/2006 | Gibson et al. | |
| 2006/0156851 A1* | 7/2006 | Jacobsen | B25J 18/06 74/490.01 |
| 2006/0241414 A1 | 10/2006 | Nowlin et al. | |
| 2006/0258938 A1 | 11/2006 | Hoffman et al. | |
| 2007/0197939 A1 | 8/2007 | Wallace et al. | |
| 2007/0225787 A1 | 9/2007 | Simaan et al. | |
| 2008/0033240 A1 | 2/2008 | Hoffman et al. | |
| 2008/0065105 A1* | 3/2008 | Larkin | A61B 1/00087 606/130 |
| 2008/0065108 A1 | 3/2008 | Diolaiti | |
| 2008/0071288 A1 | 3/2008 | Larkin et al. | |
| 2008/0114492 A1 | 5/2008 | Miegel et al. | |
| 2008/0179301 A1 | 7/2008 | Garty et al. | |
| 2008/0181473 A1 | 7/2008 | Garty et al. | |
| 2008/0188800 A1 | 8/2008 | Bencini et al. | |
| 2008/0243063 A1 | 10/2008 | Camarillo | |
| 2008/0243064 A1 | 10/2008 | Stahler et al. | |
| 2008/0243106 A1 | 10/2008 | Coe et al. | |
| 2008/0245173 A1 | 10/2008 | Schwerin et al. | |
| 2008/0249536 A1 | 10/2008 | Stahler et al. | |
| 2008/0262513 A1 | 10/2008 | Stahler et al. | |
| 2008/0302200 A1 | 12/2008 | Tobey | |
| 2009/0054222 A1 | 2/2009 | Zhang et al. | |
| 2009/0076476 A1 | 3/2009 | Barbagli et al. | |
| 2009/0076521 A1 | 3/2009 | Hansen | |
| 2009/0088774 A1 | 4/2009 | Swarup et al. | |
| 2009/0171151 A1 | 7/2009 | Choset et al. | |
| 2009/0216083 A1 | 8/2009 | Durant et al. | |
| 2009/0275818 A1 | 11/2009 | Rau et al. | |
| 2009/0275857 A1 | 11/2009 | Cabiri et al. | |
| 2010/0010504 A1 | 1/2010 | Simaan et al. | |
| 2010/0011900 A1 | 1/2010 | Burbank | |
| 2010/0030377 A1 | 2/2010 | Unsworth | |
| 2010/0069719 A1 | 3/2010 | Wehrheim | |
| 2010/0076269 A1 | 3/2010 | Makower et al. | |
| 2010/0079308 A1 | 4/2010 | Fabre et al. | |
| 2010/0099951 A1 | 4/2010 | Laby et al. | |
| 2010/0125165 A1 | 5/2010 | Troii et al. | |
| 2010/0152899 A1 | 6/2010 | Chang et al. | |
| 2010/0256558 A1 | 10/2010 | Olson et al. | |
| 2010/0331858 A1 | 12/2010 | Simaan et al. | |
| 2011/0015649 A1 | 1/2011 | Anvari et al. | |
| 2011/0066160 A1 | 3/2011 | Simaan et al. | |
| 2011/0071541 A1 | 3/2011 | Prisco et al. | |
| 2011/0071542 A1* | 3/2011 | Prisco | A61B 34/30 606/130 |
| 2011/0071544 A1 | 3/2011 | Steger et al. | |
| 2011/0125165 A1 | 5/2011 | Simaan et al. | |
| 2011/0160569 A1* | 6/2011 | Cohen | A61B 5/06 600/424 |
| 2011/0184241 A1 | 7/2011 | Zubiagte et al. | |
| 2011/0196419 A1 | 8/2011 | Cooper | |
| 2011/0213346 A1 | 9/2011 | Morley et al. | |
| 2011/0230894 A1 | 9/2011 | Simaan et al. | |
| 2011/0306929 A1 | 12/2011 | Levesque et al. | |
| 2011/0313243 A1 | 12/2011 | Zubiate et al. | |
| 2011/0319910 A1 | 12/2011 | Roelle et al. | |

(56) References Cited

U.S. PATENT DOCUMENTS

| | | |
|---|---|---|
| 2012/0071822 A1 | 3/2012 | Romo et al. |
| 2012/0109274 A1 | 5/2012 | Simaan et al. |
| 2012/0123395 A1 | 5/2012 | Stoy et al. |
| 2012/0241576 A1 | 9/2012 | Yu |
| 2012/0253131 A1 | 10/2012 | Malkowski et al. |
| 2012/0289946 A1 | 11/2012 | Steger |
| 2013/0012928 A1 | 1/2013 | Cooper et al. |
| 2013/0023859 A1 | 1/2013 | Malkowski |
| 2013/0090763 A1 | 4/2013 | Simaan et al. |
| 2013/0096540 A1 | 4/2013 | Cooper et al. |
| 2013/0110131 A1 | 5/2013 | Madhani et al. |
| 2013/0131868 A1 | 5/2013 | Rucker et al. |
| 2013/0165869 A1 | 6/2013 | Blumenkranz et al. |
| 2013/0165945 A9 | 6/2013 | Roelle et al. |
| 2013/0178838 A1 | 7/2013 | Malkowski |
| 2013/0190741 A1 | 7/2013 | Moll et al. |
| 2013/0197539 A1 | 8/2013 | Simaan et al. |
| 2013/0218141 A1 | 8/2013 | Hinman et al. |
| 2013/0231529 A1 | 9/2013 | John et al. |
| 2013/0269109 A1 | 10/2013 | Yu |
| 2013/0274715 A1 | 10/2013 | Chan et al. |
| 2013/0289581 A1 | 10/2013 | Yeung et al. |
| 2013/0300537 A1 | 11/2013 | Bajo et al. |
| 2013/0303945 A1 | 11/2013 | Blumenkranz et al. |
| 2013/0306112 A1 | 11/2013 | Blumenkranz |
| 2013/0338433 A1 | 12/2013 | Goldman et al. |
| 2014/0058406 A1 | 2/2014 | Tsekos |
| 2014/0330432 A1 | 11/2014 | Simaan et al. |
| 2015/0073434 A1 | 3/2015 | Simaan et al. |

FOREIGN PATENT DOCUMENTS

| | | |
|---|---|---|
| WO | 2005112834 | 12/2005 |
| WO | 2008036304 | 3/2008 |
| WO | 2009094670 | 7/2009 |
| WO | 2009097461 | 8/2009 |
| WO | 2009097539 | 8/2009 |
| WO | 2009124287 | 10/2009 |
| WO | 2009140688 | 11/2009 |
| WO | 2010042611 | 4/2010 |
| WO | 2011063511 | 6/2011 |
| WO | 2012015816 | 2/2012 |
| WO | 2012049623 | 4/2012 |
| WO | 2013043804 | 3/2013 |
| WO | 2013158974 | 10/2013 |
| WO | 2013158978 | 10/2013 |
| WO | 2013158983 | 10/2013 |
| WO | 2013166293 | 11/2013 |

OTHER PUBLICATIONS

A. Bajo and N. Simaan, "Finding Lost Wrenches: Using Continuum Robots for Contact Detection and Estimation of Contact Location," 2010 IEEE International Conference on Robotics and Automation (May 3-8, 2010).

A. Bajo, and N. Simaan, Kinematics-Based Detection and Localization of Contacts Along Multisegment Continuum Robots. IEEE Transactions on Robotics 28, 2 (Apr. 2012), 291-302.

R.E. Goldman, A. Bajo, and N. Simaan, Compliant Motion Control for Continuum Robots with Intrinsic Actuation Sensing. In 2011 IEEE International Conference on Robotics and Automation (Shanghai, China, 2011), pp. 1126-1132.

Bajo, A., Dharamsi, L., Netterville, J. L., Garrett, G. C., and Simaan, N (2013). Robotic-Assisted Micro-Surgery of the Throat: the Trans-Nasal Approach. In Accepted for publication in IEEE International Conference on Robotics and Automation (ICRA'2013).

A. Kapoor, M. Li, and R. H. Taylor, "Spatial Motion Constraints for Robot Assisted Suturing using Virtual Fixtures," 2005, vol. 3750, pp. 89-96.

A. Kapoor and R.H. Taylor, A Constrained Optimization Approach to Virtual Fixtures for Multi-Handed Tasks. In IEEE International Conference on Robotics and Automation (Pasadena, CA, 2008), pp. 3401-3406.

Agrawal, V., Peine, W. J., Yao, B., and Choi, S. Control of Cable Actuated Devices using Smooth Backlash Inverse. In 2010 IEEE International Conference on Robotics and Automation (Anchorage, AK, 2010), pp. 1074-1079.

Angeles, J. Automatic Computation of the Screw Parameters of Rigid-Body Motions. Part II: Infinitesimally-Separated Positions. Journal of Dynamic Systems, Measurement, and Control 108, Mar. 1986, 32-38.

Baki, P., Szekely, G., and Kosa, G. Miniature tri-axial force sensor for feedback in minimally invasive surgery. In 2012 4th IEEE RAS & EMBS In-ternational Conference on Biomedical Robotics and Biomechatronics (BioRob) (Roma, Italy, Jun. 2012), IEEE, pp. 805-810.

Bhattacharyya, S. (2011). Motion Planning and Constraint Exploration for Robotics Surgery. Master Thesis, Vanderbilt University, Nashville, TN.

Bhattacharyya, S. & Simaan, N (2013). Characterization of Constraints in Flexible Unknown Environments. In Accepted for publication in IEEE International Conference on Robotics and Automation (ICRA'2013)

Birkfellner, W., Watzinger, F., Wanschitz, F., Ewers, R., and Bergmann, H. Calibration of tracking systems in a surgical environment. IEEE Transactions on Medical Imaging 17, 5 (Oct. 1998), 737-42.

Bokelberg, E. H., Hunt, K. H., and Ridley, P. R. Spatial Motion—I: Points of inflection and the differential geometry of screws. Mechanism and Machine Theory 27, 1 (1992), 1-15.

Burgner, J., Swaney, P. J., Rucker, D. C., Gilbert, H. B., Nill, S. T., Russell III, P. T. R., Weaver, K. D., Iii, R. J. W., Russell, P. T., and Webster, R. J. A Bimanual Teleoperated System for Endonasal Skull Base Surgery. In 2011 IEEE International Conference on In-telligent Robots and Systems (San Francisco, CA, Sep. 2011), IEEE, pp. 2517-2523.

Camarillo, D. B., Carlson, C. R., and Salisbury, J. K. Configuration Tracking for Continuum Manipulators With Coupled Tendon Drive. IEEE Transactions on Robotics 25, 4 (Aug. 2009), 798-808.

Camarillo, D. B., Milne, C. F., Carlson, C. R., Zinn, M. R., and Salisbury, J. K. Mechanics Modeling of Tendon-Driven Continuum Manipulators. IEEE Transaction on Robotics 24, 6 (2008), 1262-1273.

Camarillo, D. B., Loewke, K., Carlson, C. R., and Salisbury, J. K. Vision based 3-D shape sensing of flexible manipulators. In 2008 IEEE International Conference on Robotics and Automation (Pasadena, CA, 2008), pp. 2940-2947.

Cauberg, E. C., de la Rosette, J. J., and de Reijke, T. M. How to improve the effectiveness of transurethral resection in nonmuscle invasive bladder cancer? Current Opinion in Urology 2 19, 5 (2009), 504-510.

Chan, T. F., and Dubey, R. V. A Weighted Least-Norm Solution Based Scheme for Avoiding Joint Limits for Redundant Joint Manipulators. IEEE Transaction on Robotics and Automation 11, 2 (1995), 286-292.

Chirikjian, G. S., and Burdick, J. W. A Modal Approach to Hyper-Redundant Manipulator Kinematics. IEEE Transaction on Robotics and Au-tomation 10, 3 (1994), 343-354.

Chirikjian, G. S., and Burdick, J. W. An obstacle avoidance algorithm for hyper-redundant manipulators. In Proceedings., IEEE International Conference on Robotics and Automation (1990), IEEE Comput. Soc. Press, pp. 625-631.

Croom, J. M., Rucker, D. C., Romano, J. M., and Webster, R. J. I. Visual Sensing of Continuum Robot Shape Using Self-Organizing Maps. In 2010 IEEE International Conference on Robotics and Automation (Anchorage, AK, 2010), pp. 4591-4596.

De Luca, A., Haddadin, S., and Hirzinger, G. Collision Detection and Safe Reaction with the DLR-III Lightweight Manipulator Arm. In 2006 IEEE/RSJ International Conference on Intelligent Robots and Systems (Beijing, China, 2006), pp. 1623-1630.

De Luca, A., and Manes, C. Modeling of Robots in Contact with a Dynamic Environment. IEEE Transaction on Robotics and Automation 10, 4 (1994), 542-548.

(56) References Cited

OTHER PUBLICATIONS

Degani, A., Choset, H., Wolf, A., and Zenati, M. A. Highly Articulated Robotic Probe for Minimally Invasive Surgery. In 2006 IEEE Inter-national Conference on Robotics and Automation (Orlando, FL, USA, 2006), pp. 4167-4172.

Dimaio, S. da Vinci and Beyond. In 2010 IEEE International Conference on Robotics and Automation Workshop on Medical Cyber-Physical Systems (Anchorage, AK, 2010).

Ding, J., Goldman, R. E., Xu, K, Allen, P. K, Fowler, D. L., and Simaan, N. Design and Coordination Kinematics of an Insertable Robotic Effectors Platform for Single-Port Access Surgery. IEEE/ASME Transactions on Mechatronics (2012), 1-13.

Dupont, P., Lock, J., Itkowitz, B, and Butler, E. Design and Control of Concentric-Tube Robots. IEEE Transaction on Robotics 26, 2 (2010), 209-225.

Eberman, B. S., and Salisbury, J. K. Determination of Manipulator Contact Information from Joint Torque Measurements. In Experimental Robotics I, vol. 139. Springer, 1990, pp. 463-473.

Featherstone, R. Modeling and Control of Contact Between Constrained Rigid Bodies. IEEE Transaction on Robotics and Automation 20, 1 (2004), 82-92.

Featherstone, R, Thiebaut, S. S., and Khatib, O. A General Contact Model for Dynamically-Decoupled Force/Motion Control. In 1999 IEEE International Conference on Robotics and Automation (1999), No. May, pp. 3281-3286.

Fine, H., Wei, W., Simaan, N., "Could Robots Ever Do Retina Surgery? ," Review of Ophthalmology, vol. 17, No. 5, Issue: May 1, 2010.

Fine, H., Wei, W., Chang, S. & Simaan, N (2009). A novel dual-arm dexterous ophthalmic microsurgical robot: applications for retinal vascular cannulation and stent deployment. In American Society of Retinal Specialists, Retina Congress 2009, New York, NY, Sep. 4-Oct. 4.

Garty, G., Randers-Pehrson, G., Simaan, N., Salerno, A., A., D., J., N. et al (2007). Development of an ultrahigh-throughput robotically-based biodosimetry workstation using in-situ assays. In 13th International Congress of Radiation Research, San Francisco, California, Jul. 8-12, 2007.

Ikuta, K., Yamamoto, K., and Sasaki, K. Development of remote micro-surgery robot and new surgical procedure for deep and narrow space. In 2003 IEEE International Conference on Robotics and Automation (Taipei, Taiwan, 2003), vol. 1, IEEE, pp. 1103-1108.

J. Zhang and N. Simaan, "Optimal Design of Under-actuated Steerable Electrode Arrays for Optimal Insertions," ASME Journal on Mechanisms and Robotics, Submitted , 2010.

Goldman, R. E. (2011). Analysis, Algorithms, and Control for Intelligent Surgical Exploration and Intervention. Phd Thesis, Columbia University (graduated with distinction).

Goldman, R. E., Bajo, A., Suh, L., Benson, M. & Simaan, N (2011). Rapidly Deployable Telerobotic Slave for Transurethral Exploration and Intervention. In presented in the 2011 Annual Engineering and Urology Society annual meeting, May 14, Washington, DC.

Goldman, R. E., Bajo, A. & Simaan, N. (2013). Algorithms for Autonomous Exploration and Estimation in Compliant Environments. Robotica, 31(1), 71-88.

Goldman, R. E., Bajo, A., MacLachlan, L. S., Pickens, R., Herrell, S. D. & Simaan, N. (2013). Design and Performance Evaluation of a Minimally Invasive Telerobotic Platform for Transurethral Surveillance and Intervention. IEEE Transactions on Biomedical Engineering, 60(4), 918-925.

Gravagne, I. A., and Walker, I.D. Kinematic Transformations for Remotely-Actuated Planar Continuum Robots. In 2000 IEEE International Conference on Robotics & Automation (San Francisco, 2000), No. April, pp. 19-26.

Guthart, G., and Salisbury, K. The IntuitiveTM Telesurgery System: Overview and Application. In 2000 IEEE International Conference on Robotics and Automation (2000), pp. 618-621.

Haddadin, S., De Luca, A., and Hirzinger, G. Collision Detection and Reaction: A Contribution to Safe Physical Human-Robot Interaction. In 2008 IEEE/RSJ International Conference on Intelligent Robots and Systems (Nice, France, 2008), pp. 3356-3363.

Herrell SD, Kwartowitz DM, Milhoua PM, Galloway RL. Toward Image-Guided Robotic Surgery: System Validation. J Urol. Feb. 2009; 181(2): 783-9 Discussion 789-90. Epub Dec. 16, 2008.

Ho, S C., Hibberd, R. D., and Davies, B. L. Robot Assisted Knee Surgery. IEEE Engineering in Medicine and Thology Magazine 14, 3 (1995), 292-299.

Howell, L. L. Compliant Mechanisms. Wiley-Interscience, 2001.

Ikits, M., Brederson, J. D., Hansen, C. D., and Hollerbach, J. M. An Improved Calibration Framework for Electromagnetic Tracking Devices. In 2001 IEEE Virtual Reality (Yokohama, Japan, 2001), IEEE Comput. Soc, pp. 63-70.

J. Zhang, K. Xu, N. Simaan, and S. Manolidis, "A Pilot Study of Robot-Assisted Cochlear Implant Surgery Using Steerable Electrode Arrays," in International Conference on Medical Image Computing and Computer-Assisted Intervention (MICCAI '06), 2006, pp. 33-40.

J. Zhang, S. Manolidis, T. J. Roland, and N. Simaan, "Path Planning and Workspace Determination for Robot-Assisted Insertion of Steerable Electrode Arrays for Cochlear Implant Surgery," 2008.

J. Zhang, T. J. Roland, S. Manolidis, and N. Simaan, "Optimal Path Planning for Robotic Insertion of Steerable Electrode Arrays in Cochlear Implant Surgery," ASME Journal of Medical Devices, vol. 3, No. 1, 2009.

Zhang, J., Wei, W., Ding. J., Rolant, T.J., Manolidis, S., Simaan, N., "Inroads towards Robot-Assisted Cochlear Implant Surgery using Steerable Electrode Arrays", Otology & Neurology special issue on Cochlear Implants, doi: 10.1097/MAO.0b013e3181e7117e, 2010.

Zhang, J. (2010). Design of Steerable Electrode Arrays and Optimal Insertion Path Planning for Robot-Assisted Cochlear Implant Surgeries. Phd Thesis, Department of Mechanical Engineering, Columbia University, New York City, NY.

Jones, B. A., and Walker, I. D. Kinematics for Multisection Continuum Robots. IEEE Transactions on Robotics 22, 1 (Dec. 2006), 43-57.

K. Xu and N. Simaan, "Intrinsic Wrench Estimation and Its Performance Index for Multisegment Continuum Robots," IEEE Transactions on Robotics, vol. 26, No. 3, pp. 555-561, Jun. 2010.

Xu, K. (2009). Design, Modeling and Analysis of Continuum Robots as Surgical Assistants with Intrinsic Sensory Capabilities. Phd Thesis, Columbia University).

Xu, K., Qiu, D. & Simaan, N (2011). A Pilot Investigation of Continuum Robots as a Design Alternative for Upper Extremity Exoskeletons. In IEEE International Conference on Robotics and Biomimmetics (ROBIO'2011), pp. 656-662.

Kesner, S. B., and Howe, R. D. Design and Control of Motion Compensation Cardiac Catheters. In 2010 IEEE International Conference on Robotics and Automation (Anchorage, AK, 2010), pp. 1059-1065.

Kesner, S. B., and Howe, R. D. Force Control of Flexible Catheter Robots for Beating Heart Surgery. In 2011 IEEE International Conference on Robotics and Automation (Shanghai, China, Jan. 2011), pp. 1589-1594.

Kesner, S. B., Howe, R. D., and Member, S. Position Control of Motion Compensation Cardiac Catheters. IEEE Transaction on Robotics 27, 6 (2011), 1045-1055.

Khatib, O. A Unified Approach for Motion and Force Control of Robot Manipulators: The Operational Space Formulation. IEEE Journal of Robotics and Automation 3, 1 (1987), 43-53.

Kragic, D., Marayong, P., Li-Ming Su, Okamura, A. M., and Hager, G. D. Human-Machine Collaborative Systems for Microsurgical Applications. The International Journal of Robotics Research 24, 9 (Sep. 2005), 731-741.

Kwartowitz DM, Miga MI, Herrell SD, Galloway RL. Towards Image Guided Robotic Surgery: Multi-Arm Tracking Through Hybrid Localization. Int J Comput Assist Radiol Surg. May 2009;4(3):281-6. Epub Mar. 19, 2009.

L. B. Rosenberg, "Virtual fixtures: Perceptual tools for telerobotic manipulation," in Proceedings of IEEE Virtual Reality Annual International Symposium, 1993, pp. 76-82.

Lawson, G., Matar, N., Remacle, M., Jamart, J., and Bachy, V. Transoral robotic surgery for the management of head and neck

(56) References Cited

OTHER PUBLICATIONS tumors: learning curve. European archives of oto-rhino-laryngology : official journal of the European Federation of Oto-Rhino-Laryngological Societies (EUFOS) : affiliated with the German Society for Oto-Rhino-Laryngology—Head and Neck Surgery 268, 12 (Dec. 2011), 1795-801.

Lipkin, H., and Duffy, J. Hybrid Twist and Wrench Control for a Robotic Manipulator. Transaction of the ASME 110 (1988), 138-144.

Lock, J., and Dupont, P. E. Friction Modeling in Concentric Tube Robots. In 2011 IEEE International Conference on Robotics and Automation (Shanghai, China, Jan. 2011), pp. 1139-1146.

Lumelsky, V. J., and Cheung, E. Real-Time Collision Avoidance in Tele-operated Whole-Sensitive Robot Arm Manipulators. IEEE Transactions on Systems, Man, and Cybernetics 23, 1 (1993), 194-203.

M. Li and R. H. Taylor, "Spatial Motion Constraints in Medical Robot Using Virtual Fixtures Generated by Anatomy," 2004, pp. 1270-1275.

Ma, S., and Konno, M. An obstacle avoidance scheme for hyperredundant manipulators-global motion planning in posture space. In Proceedings of Inter-national Conference on Robotics and Automation (1997), vol. 1, IEEE, pp. 161-166.

Mahvash, M., and Okamura, A. M. Friction Compensation for a Force-Feedback Telerobotic System. In 2006 IEEE International Conference on Robotics and Automation (Orlando, FL, 2006), No. May, pp. 3268-3273.

Mahvash, M., and Dupont, P. E. Mechanics of dynamic needle insertion into a biological material. IEEE transactions on biomedical engineering 57, 4 (Apr. 2010), 934-43.

Mahvash, M., and Dupont, P. E. Stiffness Control of Surgical Continuum Manipulators. IEEE Transaction on Robotics 27, 2 (2011), 334-345.

Mason, M. T. Compliance and Force Control for Computer Controlled Manipulators. IEEE Transaction on Systems, Man, and Cybernetics smc-11, 6 (1981), 418-432.

Mason, M. T., and Salisbury, J. K. Robot Hands and the Mechanics of Manipulation. MIT Press, Cambridge, MA, 1985.

Matsumoto, T., and Kosuge, K. Collision Detection of Manipulator Based on Adaptive Control Law. In 2001 IEEE/ASME International Conference on Advanced Intelligent Mechatronics (Como, Italy, 2001), pp. 177-182.

N. Simaan, R. Taylor, and P. Flint, "A Dexterous System for Laryngeal Surgery—Multi-Backbone Bending Snake-like Slaves for Teleoperated Dexterous Surgical Tool Manipulation." pp. 351-357, 2004.

N. Simaan, R. Taylor, P. Flint, and A. Hillel, "Minimally Invasive Surgery of the Upper Airways: Addressing the Challenges of Dexterity Enhancement in Confined Spaces," Nova Scien, R. Faust, Ed. 2007, pp. 261-280.

N. Simaan, W. Wei, R. Goldman, H. Fine, and S. Chang, "A Dual-Arm Workstation for Intraocular Dexterity-Enhanced Microsurgery of the Eye and In-Organ Dexterity Enhancement and Manipulation of Suspended Organs," 2006.

N. Simaan and M. Shoham, "Geometric Interpretation of the Derivatives of Parallel Robot's Jacobian Matrix with Application to Stiffness Control" ASME Journal of Mechanical Design, vol. 125, pp. 33-42., doi: 10.1115/1.1539514, 2003.

N. Simaan and M. Shoham, "Singularity Analysis of a Class of Composite Serial In-Parallel Robots," IEEE transactions on Robotics and Automation, vol. 17, No. 3, pp. 301-311, doi:10.1109/70.938387 Jun. 2001.

N. Simaan and M. Shoham, "Stiffness Synthesis of a Variable Geometry Six Degrees-of-Freedom Double Planar Parallel Robot," International Journal of Robotics Research (IJRR), vol. 22, No. 9, pp. 757-775, doi: 10.1177/02783649030229005, Sep. 2003.

N. Simaan, K. Xu, W. Wei, A. Kapoor, P. Kazanzides, R. Taylor, P. Flint, "Design and Integration of a Telerobotic System for Minimally Invasive Surgery of the Throat," International Journal of Robotics Research (IJRR) special issue on medical robotics. doi: 10.1177/0278364908104278, vol. 28, No. 9, 1134-1153 , 2009.

Simaan, N., Manolidis, S. & Roland, J. T (2009). Inroads towards a robotically inserted CI electrode development. In 9th European Symposium of Paediatric Cochlear Implantation.

Simaan, N., Zhang, J., Roland, J. T. & Manolidis, S (2010). Steerable Continuum Robot Design for Cochlear Implant Surgery. In IEEE International Conference on Robotics and Automation Workshop on Snakes, Worms and Catheters: Continuum and Serpentine Robots for Minimally Invasive Surgery, May 3.

Simaan, N., Zhang, J., Roland, J. T. & Manolidis, S (2010). Robotic Study Shows that Insertion Speed Affects Cochlear Implant Electrode Insertion Forces. In the 11th International Conference on Cochlear Implants and other Implantable Auditory Technologies, Stockholm, Sweden, Jun. 30-Jul. 3.

Simaan, N., Zhang, J., Roland, J. T. & Manolidis, S (2011). Robotic System for Steerable Cochlear Implant Insertion. In 2011 National Congress of the Italian Society of Audiology & Phoniatrics in Bari, Italy.

Simaan, N (2012). Design Considerations and Lessons Learned in Developing Systems for Single Port Access Surgery and Natural Orifice Surgery. In 34th international Conference on Engineering in Medicine and Biology Society (mini-symposium on Robotic Single-Port Surgery and Notes). San Diego, Aug. 27-31, 2012.

Simaan, N., Bajo, A., Reiter, A., Long, W., Allen, P. & Fowler, D. (2013). Lessons learned using the insertable robotic effector platform (IREP) for single port access surgery. Journal of Robotic Surgery.

Nakamura, Y. Advanced Robotics: Redundancy and Optimization. Addison-Wesley Longman Publishing Co., Inc., Boston, MA, USA, 1990.

Park, J., and Khatib, O. Robot Multiple Contact Control. Robotica 26, 05 (2008), 667-677.

Penning, R. S., Jung, J., Borgstadt, J. A., Ferrier, N. J., and Michael, R. Towards Closed Loop Control of a Continuum Robotic Manipulator for Medical Applications. In 2011 IEEE International Conference on Robotics and Automation (Shanghai, China, 2011), pp. 4822-4827.

Petrovskaya, A., Park, J., and Khatib, O. Probabilistic Estimation of Whole Body Contacts for Multi-Contact Robot Control. In 2007 IEEE International Conference on Robotics and Automation (Rome, 2007), No. c, pp. 568-573.

Phee, S. J., Low, S. C., Sun, Z. L, Ho, K. Y., Huang, W. M., and Thant, Z. M. Robotic system for no-scar gastrointestinal surgery. The international journal of medical robotics + computer assisted surgery : MRCAS 4, 1 (Mar. 2008), 15-22.

Piccigallo, M., Scarfogliero, U., Quaglia, C., Petroni, G., Val-dastri, P., Menciassi, A., and Dario, P. Design of a Novel Bimanual Robotic System for Single-Port Laparoscopy. IEEE/ASME Transaction on Mechatronics 15, 6 (2010), 871-878.

Pile, J., Tsay, I. A., Dalton, J., Balachandran, R., Labadie, R. F. & Simaan, N (2012). Speed Dependence of Insertion Forces During CI Electrode Insertion. In Presented at the 12th Annual Conference on Cochlear Implants and other Implantable Auditory Technologies CI'2012, Baltimore, MD, May 3-5, 2012.

Pile, J. & Simaan, N (2013). Characterization of Friction and Speed Effects and Methods for Detection of Cochlear Implant Electrode Tip Fold-over. In Accepted for publication in IEEE International Conference on Robotics and Automation (ICRA'2013).

R.H. Sturges Jr and S. Laowattana, "A flexible, tendon-controlled device for endoscopy," 1991, vol. 3, pp. 2582-2591.

Raibert, M. H., and Craig, J. J. Hybrid Position/Force Control of Manipulators. Journal of Dynamic Systems, Measurement, and Control 103, 2 (1981), 126.

Reichert, S., Zhang, J., Xu, K, Simaan, N. & Manolidis, S (2007). Robotic insertion of cochlear implant electrodes to minimize cochlear trauma. In 6th European Congress of Oto-Rhino-Laryngology, Head and Neck Surgery., Vienna, Austria, Jun. 2007.

Robinson, G., and Davies, J. Continuum robots—a state of the art. In 1999 IEEE International Conference on Robotics and Automation (Detroit, MI, USA, 1999), vol. 4, Ieee, pp. 2849-2854.

(56) References Cited

OTHER PUBLICATIONS

Roland J. T., Zhang, J., Manolidis, S. & Simaan, N (2009). Progress Towards a Robotically Inserted Cochlear Implant Electrode. In 12th Symposium on Cochlear Implants in Children, Seattle,.

Rosenberg, L. Virtual fixtures: Perceptual tools for telerobotic manipulation. In Proceedings of IEEE Virtual Reality Annual International Symposium (1993) pp. 76-82.

Rucker, D. C., and Webster, III, R. J. Deflection-Based Force Sensing for Continuum Robots: A Probabilistic Approach. In 2011 IEEE/RSJ Inter-national Conference on Intelligent Robots and Systems (2011), pp. 3764-3769.

Rucker, D. C., Jones, B. A., and Webster III, R. J. A Geometrically Exact Model for Externally Loaded Concentric-Tube Continuum Robots. IEEE Transaction on Robotics 26, 5 (2010), 769-780.

S. J. Harris, W. J. Lin, R. D. Hibberd, J. Cobb, R. Middelton, and B. L. Davies, "Experiences with Robotic Systems for Knee Surgery," vol. 1205, J. Troccaz, E. Grimson, and R. Mosges, Eds. Springer, 1997, pp. 757-766.

Saito, S. Transurethral en bloc resection of bladder tumors. The Journal of urology 166,6 (Dec. 2001), 2148-50.

Salerno, A., Zhang, J., Bhatla, A., Lyulko, O. V., Nie, J., Dutta, A. et al (2007). Design Considerations for a Minimally Invasive High-Throughput Automation System for Radiation Biodosimetry. In IEEE Conference on Automation Science and Engineering, pp. 846-852. Scottsdale, AZ, USA.

Salisbury, J. Active stiffness control of a manipulator in cartesian coordinates. In 1980 19th IEEE Conference on Decision and Control including the Symposium on Adaptive Processes (1980), pp. 95-100.

Seibold, U., Kubler, B., and Hirzinger, G. Prototype of Instrument for Minimally Invasive Surgery with 6-Axis Force Sensing Capability. In Proceedings of the 2005 IEEE International Conference on Robotics and Automation (Barcelona, Spain, 2005), 496-501, Ed., IEEE, pp. 496-501.

Sentis, L., Park, J., and Khatib, O. Compliant Control of Multicontact and Center-of-Mass Behaviors in Humanoid Robots. IEEE Transactions on Robotics 26, 3 (Jun. 2010), 483-501.

Shen, J.-H., Yu, H., Simaan, N. & Joos, K. M. (2013). A Robotic-controlled Intraocular OCT Probe. In 2013 The Association for Research in Vision and Ophthalmology Annual Conference (ARVO'2013).

Siciliano, B., Sciavicco, L., Villani, L., and Oriolo, G. Robotics: Modelling, Planning, and Control. 2009.

Su, H., Cardona, D. C., Shang, W., Camilo, A., Cole, G. A., Rucker, D. C., Webster, R. J., and Fischer, G. S. A MRI-Guided Concentric Tube Continuum Robot with Piezoelectric Actuation: A Feasibility Study. In 2012 IEEE International Conference on Robotics and Automation (St. Paul, MN USA, 2012), No. May.

Taylor, R., Jensen, P., Whitcomb, L., Barnes, A., Kumar, R., Stoianovici, D., Gupta, P., Wang, Z., DeJuan, E., and Kavoussi, L. A Steady-hand robotic system for microsurgical augmentation. International Journal of Robotics Research 18, 12 (1999), 1201-1210.

Torres, L. G., and Alterovitz, R. Motion Planning for Concentric Tube Robots Using Mechanics-based Models. In 2011 IEEE/RSJ International Con-ference on Intelligent Robots and Systems (San Francisco, CA, USA, 2011), pp. 5153-5159.

Ukai, R., Kawashita, E., and Ikeda, H. A new technique for transurethral resection of superficial bladder tumor in 1 piece. The Journal of Urology2 163, 3 (2000), 878-879.

Valdastri, P., Harada, K., Menciassi, A., Beccai, L., Stefanini, C., Fujie, M., and Dario, P. Integration of a miniaturised triaxial force sensor in a minimally invasive surgical tool. IEEE transactions on biomedical engineering 53, 11 (Nov. 2006), 2397-400.

W. Wei, R. Goldman, H. Fine, S. Chang, and N. Simaan, "Design and Dexterity Evaluation for a Dual-Arm Micro-Surgical Robotic System for Orbital Manipulation and Intraocular Dexterity," IEEE Transactions on Robotics, vol. 25, No. 1, pp. 147-157, 2009.

Wagner, C. R., Stylopoulos, N., Jackson, P. G., and Howe, R. D. The Benefits of Force Feedback in Surgery: Examination of Blunt Dissection. Presence: Teleoperators and Virtual Environments 16, 3 (2007), 252-262.

Webster III, R. J., Romano, J. M., and Cowan, N. J. Mechanics of Precurved-Tube Continuum Robots. IEEE Transaction on Robotics 25, 1 (2009), 67-78.

Webster III, R. J., and Jones, B. A. Design and Kinematic Modeling of Constant Curvature Continuum Robots: A Review. The International Journal of Robotics Research (Jun. 2010).

Wei Tech, A., Khosla, P., and Riviere, C. An Intelligent Hand-Held Microsurgical Instrument for Improved Accuracy. In 23rd Annual International Conference of the IEEE Engineering in Medicine and Biology Society (Istanbul, Turkey, 2001), pp. 25-28.

Wei, W., Goldman, R., Fine, H., Chang, S., Simaan, N., "Performance Evaluation for Multi-Arm Manipulation of Hollow Suspended Organs," IEEE Transactions on Robotics, vol. 25, No. 1, pp. 147-157, doi 10.1109/TRO.2008.2006865, 2009.

Wei, W., Simaan N., "Design of Planar Parallel Robots With Preloaded Flexures for Guaranteed Backlash Prevention," ASME Journal of Mechanisms and Robotics (JMR), doi:10.1115/1.4000522, vol. 2, No. 1, pp. 011012-1 to 011012-10, 2010.

Wei, W. (2010). Design and Implementation of High-Precision Hybrid Robotic Systems with Application for Ophthalmic Micro-Surgery. Phd Thesis, Department of Mechanical Engineering, Columbia University, New York City, NY.

Wei, W., Fine, H., Chang, S. & Simaan, N (2010). A Pilot Study on Using a Flexible Cannula Robot for Micro-Vascular Stenting. In IEEE International Conference on Robotics and Automation Workshop on Snakes, Worms and Catheters: Continuum and Serpentine Robots for Minimally Invasive Surgery, IEEE International Conference on Robotics and Automation, May 3.

Weinstein, G. S., O'Malley, B. W., Magnuson, J. S., Carroll, W. R., Olsen, K. D., Daio, L., Moore, E. J., and Holsinger, F. C. Transoral robotic surgery: A multicenter study to assess feasibility, safety, and surgical margins. The Laryngoscope (Jul. 2012), 1-7.

Whitney, D. E. Force Feedback Control of Manipulator Fine Motions. Journal of Dynamic Systems, Measurement, and Control 99, 2 (1977), 91.

Whitney, D. E. Resolved Motion Rate Control of Manipulators and Human Prostheses. IEEE Transaction on Man-Machine Systems MMS-10, 2 (Jun. 1969), 47-53.

Yoshikawa, T. Force Control of Robot Manipulators. In 2000 IEEE International Conference on Robotics and Automation (San Francisco, CA, USA, 2000), No. April, pp. 220-226.

Yu, H., Shen, J. H., Joos, K. M. & Simaan, N (2013). Design , Calibration and Preliminary Testing of A Robotic Telemanipulator for OCT guided Retinal Surgery. In Accepted for publication in IEEE International Conference on Robotics and Automation (ICRA'2013).

Thou, J., Shen, X., Petriu, E. M., and Georganas, N. D. Linear Velocity and Acceleration Estimation of 3 DOF Haptic Interface. In IEEE International Workshop on Haptic Audio Visual Environments and their Application (HAVE 2008) (Ottawa, Canada, 2008), pp. 137-142.

W. Wei, K. Xu, and N. Simaan, "A compact Two-armed Slave Manipulator for Minimally Invasive Surgery of the Throat," in IEEE RAS/EMBS International Conference on Biomedical Robotics and Biomechatronics, 2006, pp. 769-774.

Wei, W., Goldman, R. E., Simaan, N., Fine, H. & Chang, S (2007). Design and Theoretical Evaluation of Micro-Surgical Manipulators for Orbital Manipulation and Intraocular Dexterity. In 2007 IEEE International Conference on Robotics and Automation, pp. 3389-3395. Roma, Italy.

Wei, W., and Simaan, N. Modeling, Force Sensing, and Control of Flexible Cannulas for Microstent Delivery. Journal of Dynamic Systems, Measurement, and Control 134, 4 (2012), 041004.

Wei, W., Popplewell, C., Fine, H., Chang, S., Simaan, N., "Enabling Technology for Micro-Vascular Stenting in Ophthalmic Surgery," ASME Journal of Medical Devices (JMED), vol. 4, Issue 1, 014503 (6 pages) doi:10.1115/1.4001193, 2010.

U.S. Office action for U.S. Appl. No. 13/891,389 dated Jan. 2, 2015.

(56) References Cited

OTHER PUBLICATIONS

U.S. Office action for U.S. Appl. No. 14/271,418 dated May 20, 2015.
Bajo, A., Goldman, R. E., Wang, L., Fowler, D. & Simaan, N (2012). Integration and Preliminary Evaluation of an Insertable Robotic Effectors Platform for Single Port Access Surgery. In International Conference on Robotics and Automation (ICRA'2012), pp. 3381-3387.
Bajo, A., Pickens, R. B., Herrell, D. S. & Slmaan, N (2012). A Pilot Ex-Vivo Evaluation of a Telerobotic System for Transurethral Intervention and Surveillance. In Hamlyn Symposium on Medical Robotics.
Bajo, A., Pickens, R. B., Herrell, D. S. & Simaan, N (2013). Constrained Motion Control of Multisegment Continuum Robots for Transurethral Bladder Resection and Surveillance. In Accepted for publication in IEEE International Conference on Robotics and Automation (ICRA'2013).
A. Kapoor, K. Xu, W. Wei, N. Simaan, and R. Taylor, "Telemanipulation of Snake-Like Robots for Minimally Invasive Surgery of the Upper Airway," in MICCAI 2006 workshop on medical robotics, 2006.
A. Kapoor, N. Simaan, and P. Kazanzides, "A System for Speed and Torque Control of DC Motors with Application to Small Snake Robots," 2004.
A. Kapoor, N. Simaan, and R. Taylor, "Suturing in Confined Spaces: Constrained Motion Control of a Hybrid 8-DoF Robot", in IEEE Conference on Advanced Robotics, 2005, pp. 452-459.
Abbott, J., Marayong, P., and Okamura, A. M. Haptic virtual fixtures for robot-assisted manipulation. Robotics Research 28, Aug. 2007, 49-64.
Alexander T. Hillel, Ankur Kapoor, Nabil Simaan, Russell H. Taylor and Paul Flint, "Applications of Robotics for Laryngeal Surgery," Otolaryngologic Clinics of North America, Nasir Bhatti & Ralph P. Tufano Eds., vol. 41, Issue 4, pp. 781-791, doi:0.1016/j.otc.2008.01.021, Aug. 2008.
Chen, Y., Zhang, J., Wang, H., Garty, G., Xu, Y., Lyulko, O., Turner, H., Randers-Pehrson, G., Simaan, N., Yao, L., Brenner, D., "Development of a Robotically-based Automated Biodosimetry Tool for Highthroughput Radiological Triage," accepted in International Journal of Biomechatronics and Biomedical Robotics (IJBBR), vol. 1, No. 2 pp. 115-125, 2010.
Debus, T., Dupont, P., and Howe, R. Contact State Estimation using Multiple Model Estimation and Hidden Markov Models. 2The International Journal of Robotics Research 23, 4-5 (2004), 399-413.
Ding, J., Xu, K., Goldman, R. E., Allen, P. K, Fowler, D. L., and Simaan, N. "Design, Simulation and Evaluation of Kinematic Alternatives for Insertable Robotic Effectors Platforms in Single Port Access Surgery," In 2010 IEEE International Conference on Robotics and Automation (Anchorage, AK, 2010), pp. 1053-1058.
Godage, Isuru S. et al., "Shape Function-Based Kinematics and Dynamics for Variable Length Continuum Robotic Arms," 2011 IEEE International Conference on Robotics and Automation (May 9-13, 2011).
R. E. Goldman, A. Bajo, and N. Simaan, "Compliant Motion Control for Continuum Robots with Intrinsic Actuation Sensing," in IEEE International Conference on Robotics and Automation, 2011, pp. 1126-1132.
Gravagne, Ian A. and Ian D. Walker, "Manipulability, Force, and Compliance Analysis for Planar Continuum Manipulators," IEEE Transactions on Robotics and Automation, vol. 18, No. 3 (Jun. 2002).
Gravagne, Ian A. et al, "Good Vibrations: A Vibration Damping Setpoint Controller for Continuum Robots," Proceedings of the 2001 IEEE International Conference on Robotics & Automation (May 21-26, 2001).
Hamid, S. A. & Simaan, N (2009). Design and Synthesis of Wire-Actuated Universal-Joint Wrists for Surgical Applications. In 2009 IEEE International Conference on Robotics and Automation, pp. 1807-1831. Kobe, Japan.
Hannan, M. W., and Walker, I. D. Kinematics and the Implementation of an Elephant's Trunk Manipulator and Other Continuum Style Robots. Journal of Robotic Systems 20, 2 (2003), 45-63.
Hayward, Vincent, "Fast Collision Detection Scheme by Recursive Decomposition of a Manipulator Workspace," Proceedings IEEE International Conference on Robotics and Automation, vol. 3 (1986).
Hogan, N. Impedance Control: An Approach to Manipulation: Part ITheory. Journal of Dynamic Systems, Measurement, and Control 107, 1 (1985), 1.
International Search Report and Written Opinion for PCT Application No. PCT/US2013/021167 dated Mar. 22, 2013.
International Search Report and Written Opinion for PCT Application No. PCT/US2013/037336 dated Jul. 25, 2013.
International Search Report and Written Opinion for PCT Application No. PCT/US2013/037346 dated Aug. 27, 2013.
International Search Report and Written Opinion for PCT Application No. PCT/US2013/037353 dated Aug. 19, 2013.
International Search Report and Written Opinion for PCT Application No. PCT/US2013/039280 dated Aug. 20, 2013.
J. Ding, K. Xu, R. Goldman, P. Allen, D. Fowler, and N. Simaan, "Design, Simulation and Evaluation of Kinematic Alternatives for Insertable Robotic Effectors Platforms in Single Port Access Surgery." pp. 1053-1058, 2010.
J. J. Abbott and A. M. Okamura, "Stable Forbidden-Region Virtual Fixtures for Bilateral Telemanipulation," vol. 128, No. 1, pp. 53-64, 2006.
J. Zhang, S. Bhattacharyya, and N. Simaan, "Model and Parameter Identification of Friction During Robotic Insertion of Cochlear-Implant Electrode Arrays," in IEEE International Conference on Robotics and Automation, 2009, pp. 3859-3864.
Jones, Bryan A., "Kinematics for Multisection Continuum Robots," IEEE Transactions on Robotics, vol. 22, No. 1 (Feb. 2006).
K. Xu and N. Simaan, "Actuation Compensation for Flexible Surgical Snake-like Robots with Redundant Remote Actuation," in IEEE International Conference on Robotics and Automation, 2006, pp. 4148-4154.
K. Xu and N. Simaan, "Analytic Formulation for Kinematics, Statics and Shape Restoration of Multibackbone Continuum Robots via Elliptic Integrals," ASME Journal of Mechanisms and Robotics (JMR), vol. 2, pp. 11006-11013, 2010.
K. Xu, R. Goldman, J. Ding, P. Allen, D. Fowler, and N. Simaan, "System Design of an Insertable Robotic Effector Platform for Single Port Access (SPA) Surgery," in IEEE/RSJ International Conference on Intelligent Robots and Systems, 2009, pp. 5546-5552.
K. Xu and N. Simaan, "An Investigation of the Intrinsic Force Sensing Capabilities of Continuum Robots," IEEE Transactions on Robotics (TRO), vol. 23, No. 3 (Jun. 2008).
Mahvash, Mohsen and Pierre E. Dupont, "Stiffness Control of a Continuum Manipulator in Contact with a Soft Environment," The 2010 IEEE/RSJ International Conference on Intelligent Robots and Systems (Oct. 18-22, 2010).
Mahvash, Mohsen and Pierre E. Dupont, "Stiffness Control of Surgical Continuum Manipulators," IEEE Transactions on Robotics, vol. 27, No. 2 (Apr. 2011).
N. Simaan, A. Bajo, A. Reiter, L. Wang, P. Allen, and D. Fowler, "Lessons learned using the insertable robotic effector platform (IREP) for single port access surgery," Journal of Robotic Surgery, Apr. 2013.
N. Simaan, "Snake-Like Units Using Flexible Backbones and Actuation Redundancy for Enhanced Miniaturization," In 2005 IEEE International Conference on Robotics and Automation (Barcelona, Spain, 2005), IEEE, pp. 3023-3028.
N. Simaan, Russell H. Taylor, Paul Flint, "High Dexterity Snake-like Robotic Slaves for Minimally Invasive Telesurgery of the Upper Airway," MICCAI 2004 (7th International Conference on Medical Image Computing and Computer-Assisted Intervention), pp. 17-24, vol. 2, Saint Malo, France, Sep. 26-30, 2004.
Simaan, N., Glozman, D. & Shoham, M (1998). Design Considerations of New Six Degrees-Of-Freedom Parallel Robots. In IEEE International Conference on Robotics and Automation (ICRA'1998), pp. 1327-1333.

(56) References Cited

OTHER PUBLICATIONS

Simaan, N. (1999). Analysis and Synthesis of Parallel Robots for Medical Applications. Master Thesis, Technion-Israel Institute of Technology, Haifa, Israel.

N. Simaan, Task-Based Design and Synthesis of Variable Geometry Parallel Robots (2002). Phd Thesis, Technion-Israel Institute of Technology, Haifa, Israel.

Pickens, R. B., Bajo, A., Simaan, N. & Herrell, S. D (2012). Preliminary Testing of a Transurethral Dexterous Robotic System for Bladder Resection. In 27th EUS Annual Meeting, pp. 65. Atlanta, GA.

Pile, J., Cheung, M.-Y., Zhang, J. & Simaan, N (2011). Algorithms and Design Considerations for Robot Assisted Insertion of Perimodiolar Electrode Arrays. In 2011 IEEE International Conference on Robotics and Automation. Shanghai, China.

R. Taylor et al., "Steady-hand robotic system for microsurgical augmentation," International Journal of Robotics Research, vol. 18, No. 12, pp. 1201-1210, 1999.

Reiter, A., Bajo, A., Illiopoulos, K., Simaan, N., and Allen, P. K. Learning-Based Configuration Estimation of a Multi-Segment Continuum Robot. In The Fourth IEEE RAS/EMBS International Conference on Biomedical Robotics and Biomechatronics (Roma, Italy, 2012), p. accepted.

Reiter, A., Goldman, R. E., Bajo, A., Illiopoulos, K., Simaan, N., and Allen, P. K. A Learning Algorithm for Visual Pose Estimation of Continuum Robots. In 2011 IEEE/RSJ International Conference on Intelligent Robots and Systems (San Francisco, CA, USA, 2011), pp. 2390-2396.

Rivera-Serrano, C. M., Johnson, P., Zubiate, B., Kuenzler R., Choset, H., Zenati, M., Tully, S., and Duvvuri, U. A transoral highly flexible robot: Novel technology and application. The Laryngoscope 122, 5 (May 2012), 1067-71.

Sen, T. H., Deshmukh, N., Roger E, . . . G., Kazanzides, P., Taylor, R. H., Boctor, E. et al (2012). Enabling technologies for natural orifice transluminal endoscopic surgery (N.O.T.E.S.) using robotically guided elasticity imaging. In Proceeding of SPIE Medical Imaging 2012, pp. 83161Y1-83161Y8.

Tully, S., Bajo, A., Kantor, G., Choset, H., and Simaan, N. Constrained Filtering with Contact Detection Data for the Localization and Registration of Continuum Robots in Flexible Environments. In 2012 IEEE International Conference on Robotics and Automation (St. Paul, MI USA, 2012).

\* cited by examiner

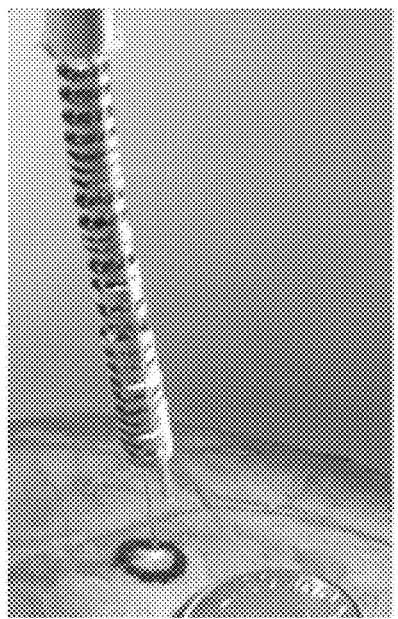 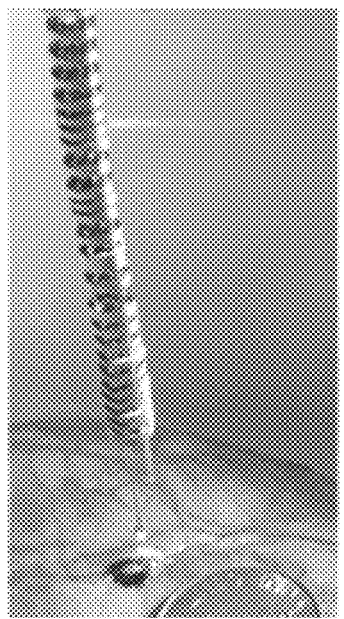 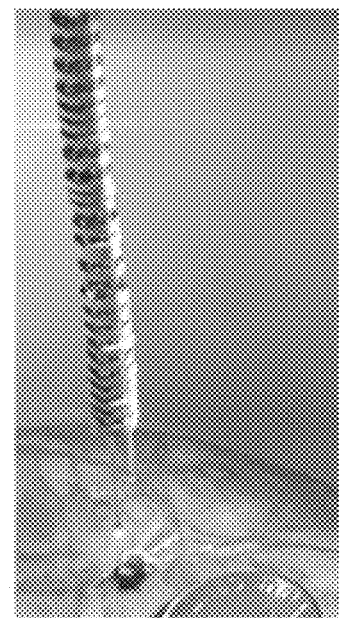
*FIG. 7A*  *FIG. 7B*  *FIG. 7C*
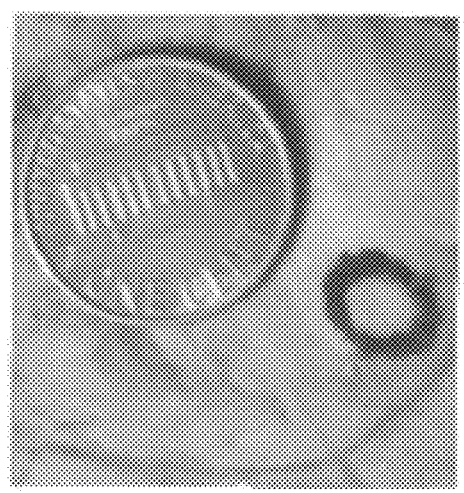 
*FIG. 7D*  *FIG. 7E*

Algorithm 1 Virtual Fixture
───────────────────────────────
Input: $\theta_1, \delta_1, \theta_2, \delta_2, q_{ins}$
Input: $\dot{\theta}_1, \dot{\delta}_1, \dot{\theta}_2, \dot{\delta}_2, \dot{q}_{ins}$
  if $q_{ins} \leq 0$ then
    $\bar{V} \leftarrow [\theta_1 \;\; 0 \;\; 0 \;\; 0 \;\; 0]^T$
    $\bar{P} \leftarrow \bar{V}(\bar{V}^T\bar{V})^\dagger \bar{V}^T$
    $P \leftarrow I - \bar{P}$
    if $(\dot{q}_{ins} < 0)$ & $(\theta_1 \leq \theta_{min} + \theta_0 \|q_{ins}\|/L_1)$ then
      $u \leftarrow (\theta_{min} + \theta_0 \|q_{ins}\|/L_1 - \theta_1)[1 \;\; 0 \;\; 0 \;\; 0 \;\; 0]^T$
    else
      $u \leftarrow [0 \;\; 0 \;\; 0 \;\; 0 \;\; 0]^T$
    end if
  else
    $\bar{P} = 0$
    $P = I$
    $u \leftarrow [0 \;\; 0 \;\; 0 \;\; 0 \;\; 0]^T$
  end if
  $\dot{\Psi}_{des} \leftarrow P\dot{\Psi}_{des} + k_d \bar{P} u$
  return $\dot{\Psi}_{des}$
───────────────────────────────

*FIG. 16*

SYSTEMS AND METHODS FOR ROBOT-ASSISTED TRANSURETHRAL EXPLORATION AND INTERVENTION

RELATED APPLICATIONS

This application claims priority to U.S. Provisional Application No. 61/840,748 filed Jun. 28, 2013, titled "SYSTEMS AND METHODS FOR ROBOT-ASSISTED TRANSURETHRAL EXPLORATION AND INTERVENTION," the entirety of which is incorporated herein by reference.

BACKGROUND

In 2010, there were 70,530 new cases of bladder cancer diagnosed in the United States and 14,680 deaths from bladder cancer. Of the newly diagnosed patients, more than 52,000 were men and 18,000 were women with most male patients above the age of 50. Approximately 70% of these new cases of bladder cancer were classified as non-muscle invasive cancer (NMIBC) which is initially treated with transurethral resection of bladder tumor (TURBT). In addition to being a standard surgical therapy for noninvasive bladder cancer, TURBT is also an integral part of the diagnostic evaluation of all bladder tumors.

FIG. 1 illustrates one example of a bladder resection procedure being performed with a resectoscope. The resectoscope is inserted through the urethra of a patient to access the bladder. Tumors in the bladder wall are resected through to the muscular layer of the bladder. Motion of the resectoscope is limited by the tissue and pubis anterior-superiorly and posterior-inferiorly. Medial and lateral motion is further hampered by the legs of the patient. The inserts in FIG. 1 depicts a tumor with both a broad front invasion in which the extent of the tumor is visible at the surface (A) and tentacular invasion in which the tumor invades below the urothelium and the margin for resection is invisible under white-light based imaging (B).

TURBT does, however, have its shortcomings. Initial TURBT is associated with imperfect clinical staging and incomplete tumor removal. An accurate pathological diagnosis, which is determined by depth of tumor invasion, is crucial for staging urothelial carcinomas. The stage of a patient's bladder cancer plays a key role in determining the patient's treatment and prognosis. The urologist is responsible for accurately sampling bladder tissue for evaluation, and should include muscularis propria (detrusor muscle) for adequate staging. Specimens missing muscle layers cannot confirm complete tumor resection.

The technical challenges of manual TURBT procedures are associated with considerable clinical ramifications. Although TURBT remains the gold standard for initial diagnosis and treatment of NMIBC, the early recurrence rate at three months can be as high as 45%. Furthermore, despite recommendations to perform complete resection of all visible tumors during an initial TURBT, a study of 150 consecutive patients with NMIBC undergoing repeat transurethral resection within 6 weeks of the initial procedure found 76% with residual tumor. Studies also indicate that at up to 5% of all TUR procedures result in perforations in the bladder due to full wall resection.

Furthermore, there is high variability in the clinical outcomes of TURBT procedures based on the skill of the surgeon and the technique used. In a combined analysis of seven randomized studies, the recurrence rate following TURBT for non-muscle invasive bladder cancer varied between institutions from 7% to 45%. This and other studies have been unable to attribute this variation to any other factor and instead conclude that the high variability in success rate is attributable to surgeon technique.

Lesion location can also influence resectability of tumors. In certain areas of the bladder, the ideal angle of approach to a tumor may be kinematically infeasible such that the bladder wall cannot be appropriately reached or traced. As illustrated in FIG. 1, the anatomic constraints of the entrance through the urethra make access to anterior regions of the bladder difficult or infeasible without external manipulation. For approaching anterior aspects of the bladder, suprapubic pressure is applied to bring the bladder wall into the reachable workspace of the rigid resectoscope. However, these techniques have limited success with many patients—particularly in obese patients due to thick fat layers.

SUMMARY

International Publication No. WO 2013/106664 to Simaan et al., the entirety of which is incorporated herein by reference, describes systems and methods for reliable transurethral access to surfaces within the bladder. Embodiments also provide for improved surveillance and visual feedback to a surgeon or other user of the device and for mechanisms to prevent robotic tools from causing damage to the interior of the bladder.

In some constructions, the invention provides a robotic device for transurethral procedures in the bladder. The robotic device includes a central stem, a dexterous arm, and an actuator system. The central stem includes a first access channel and a second access channel positioned longitudinally along the central stem. The dexterous arm is at least partially positioned within the first access channel of the central stem and includes two working channels. A first camera system is positioned within the first working channel of the dexterous arm and a working tool is insertable through the second working channel. A second camera system is positioned at least partially within the second access channel of the central stem. The actuator system is configured to controllably extend and retract the dexterous arm through the first access channel of the central stem and to controllably bend the dexterous arm to position the working tool inside the bladder.

Some constructions also provide a tool adjustment component positioned at the distal end of the dexterous arm. The tool adjustment component is controlled to adjust the angle of a working tool relative to the dexterous arm. In some embodiments, the tool adjustment component includes three circular segments arranged concentrically. The first segment is connected to the second segment by a first flexure positioned near an edge of the first segment and the second segment. The first flexure allows the second segment to be controllably tilted relative to the first segment on a first axis. The second segment is connected to the third segment by a second flexure positioned near an edge of the second segment and an edge of the third segment. The second flexure allows the second segment to be controllably tilted relative to the second segment on a second axis. The second axis is substantially perpendicular to the first axis.

Another construction provides a method of performing a medical procedure on an interior surface of a bladder. A rigid central stem is inserted transurethrally into the bladder of a patient. A dexterous arm is then extended from a distal end of the rigid central stem. The dexterous arm is controllably bent to position a distal end of the dexterous arm at a target site inside the bladder. Images of the target site are then captured by a first camera positioned at the distal end of the dexterous arm and a second camera positioned at the distal end of the rigid central stem. Commands are received from a user based on the displayed images. The commands tag the boundaries of a surface area inside the bladder where the medical procedure is to be performed. The tagged boundaries are then used to define the dimensions of a virtual fixture tangential to the surface area of the bladder. The operation and position of the dexterous arm and a working tool positioned at the distal end of the dexterous arm are controlled based on operation commands received from the user. However, the operation of the working tool is restricted in locations outside of the virtual fixture. In some embodiments, the working tool is entirely prevented from operating when positioned outside of the virtual fixture.

In one embodiment, the invention provides a robotic system for procedures in a cavity. The robotic system includes a rigid central stem including an access channel positioned longitudinally along the rigid central stem and a dexterous arm at least partially positioned within the access channel of the central stem. The dexterous arm includes a plurality of individually adjustable segments. A control system receives a positioning command from a manipulator control indicative of a desired movement of a distal end of the dexterous arm. A virtual fixture is defined that is representative of the access channel of the rigid central stem. The position of the dexterous arm is adjusted such that the distal end of the dexterous arm performs the desired movement while the portion of the dexterous arm that is positioned within the first access channel is not moved beyond the defined virtual fixture.

Other aspects of the invention will become apparent by consideration of the detailed description and accompanying drawings.

BRIEF DESCRIPTION OF THE DRAWINGS

FIGS. 7A-7E are perspective views of a laser ablation tool of the robotic device of FIG. 2 performing a resection.

FIG. 16 is a flowchart illustrating a method of defining a virtual fixture used to restrict movement of the continuum robot extending from a resectoscope.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 2:
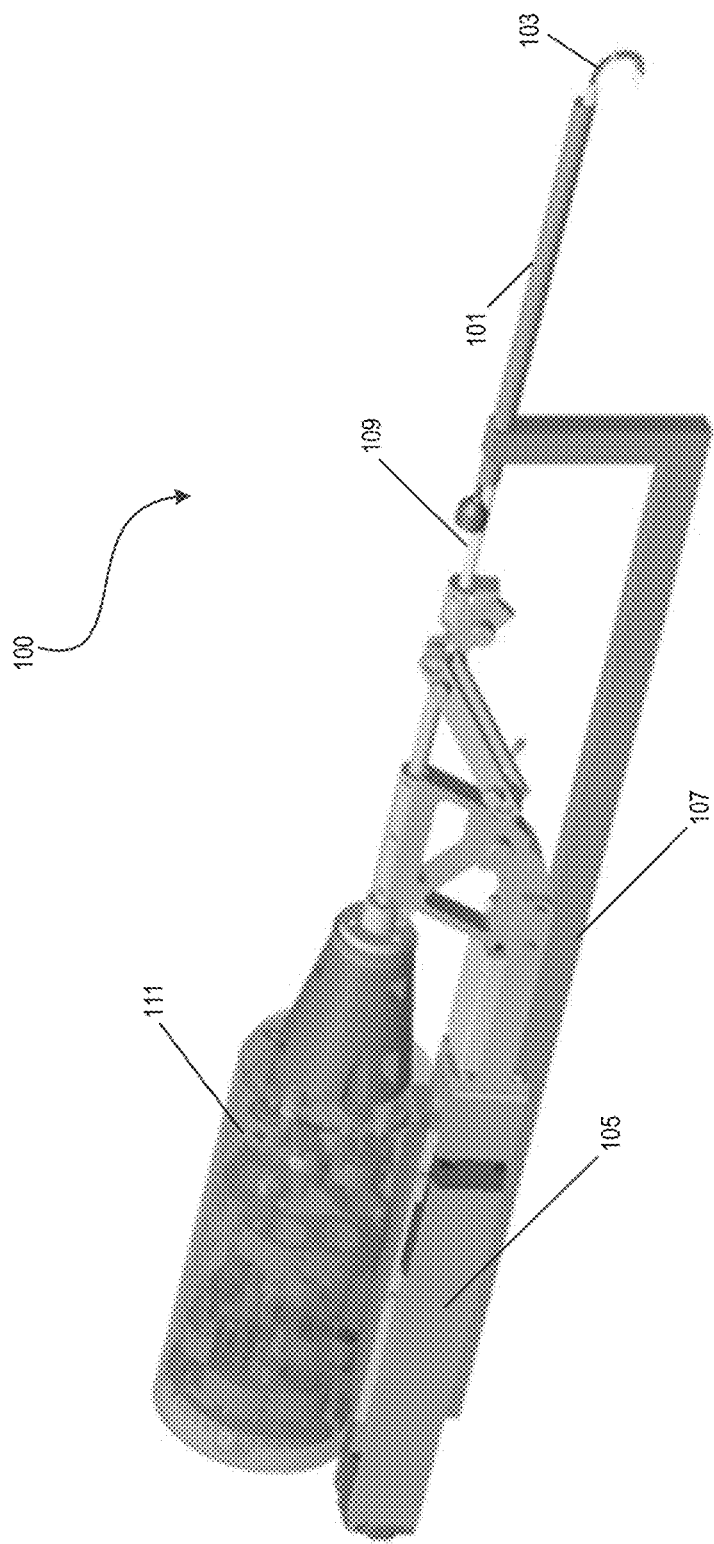
FIG. 2 is a perspective view of a robotic device for transurethral bladder procedures according to one embodiment of the present invention.

FIG. 2 illustrates an example of a robotic device 100 for performing a procedure on the interior of a cavity. In particular, FIG. 2 illustrates the robotic device 100 configured to perform a transurethral procedure on the interior of a bladder. The robotic device includes a central stem 101 and a dexterous arm 103 extending through an access channel of the central stem 101. In some constructions, the central stem 101 is a hollow rigid shaft with a single concentric access channel. However, in other constructions, such as described below, the central stem is a rigid shaft that includes multiple access channels running along the length of the shaft. Alternatively, the central stem can be constructed of a bendable material that can provide stability while also complying somewhat to forces applied to the central stem by the human anatomy during usage.

The central stem 101 is connected to a first actuator component 105 by a bracket 107. The bracket 107 ensures that the central stem 101 does not move relative to the actuator 105. The actuator 105 is mechanically coupled to a push rod 109. When the actuator 105 moves the push rod 109 forward, the dexterous arm 103 is extended from the distal end of the central stem 101. When the push rod 109 is moved backward, the dexterous arm 103 retracts into the central stem 103. A second actuator component 111 is coupled to the top surface of the first actuator component 105. The second actuator component 111 controls movement of the dexterous arm 103.

Figure 3:
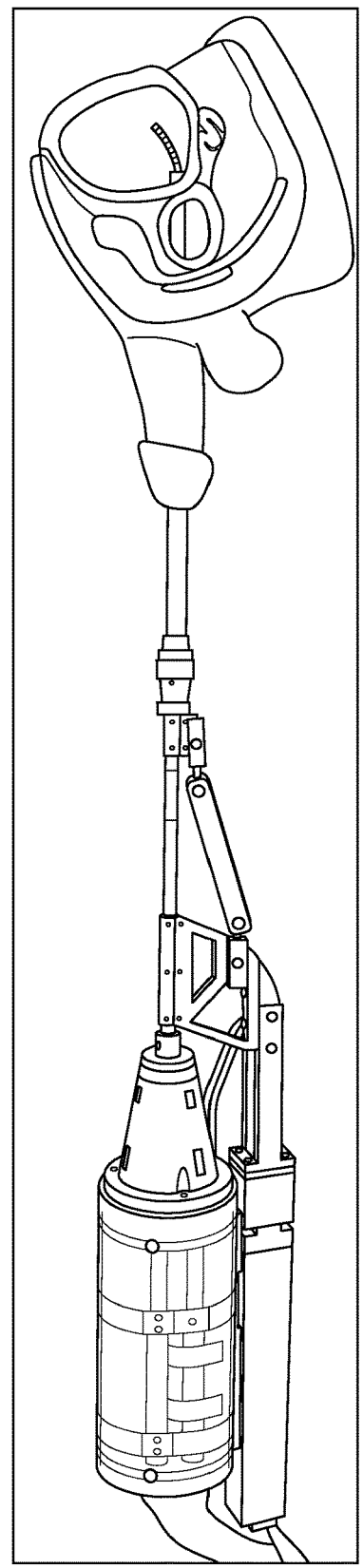
FIG. 3 is a cross-section view of the robotic device of FIG. 2 inserted into a bladder transurethrally.

The robotic device 100 is used to conduct observation of the interior of the bladder and to perform medical procedures, such as resection of tumors, on the interior surface of the bladder. With the dexterous arm 103 entirely retracted into the interior of the central stem 101, the central stem 101 is inserted through the urethra of the patient until the distal end of the central stem 101 is positioned within the bladder of the patient. After the distal end of the central stem 101 is positioned inside the bladder, the first actuator 105 extends the dexterous arm 103 out of the central stem 101. The second actuator system 111 can then move or bend the dexterous arm 103 to position the distal end of the dexterous arm 103 at a target site within the bladder. This controllable bending allows a working tool (such as those described in detail below) to be easily placed at target sites that historically have been difficult to reach with a rigid resectoscope, such as, for example, the anterior surface of the bladder. FIG. 3 illustrates the robotic device inserted into bladder of a patient transurethrally with the dexterous arm extended.

Robotic devices that include actuators for extending a dexterous arm from a central stem and for adjusting the position of the extended dexterous arm have previously been described in International Publication No. WO 2012/015816.

Figure 5:
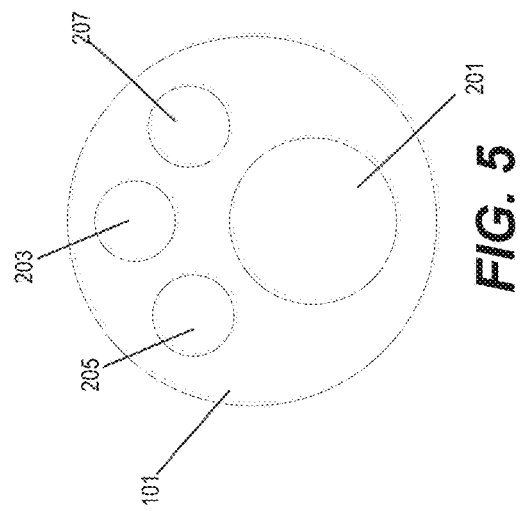
FIG. 5 is a cross-sectional view of a central stem of the robotic device of FIG. 2.
Figure 4:
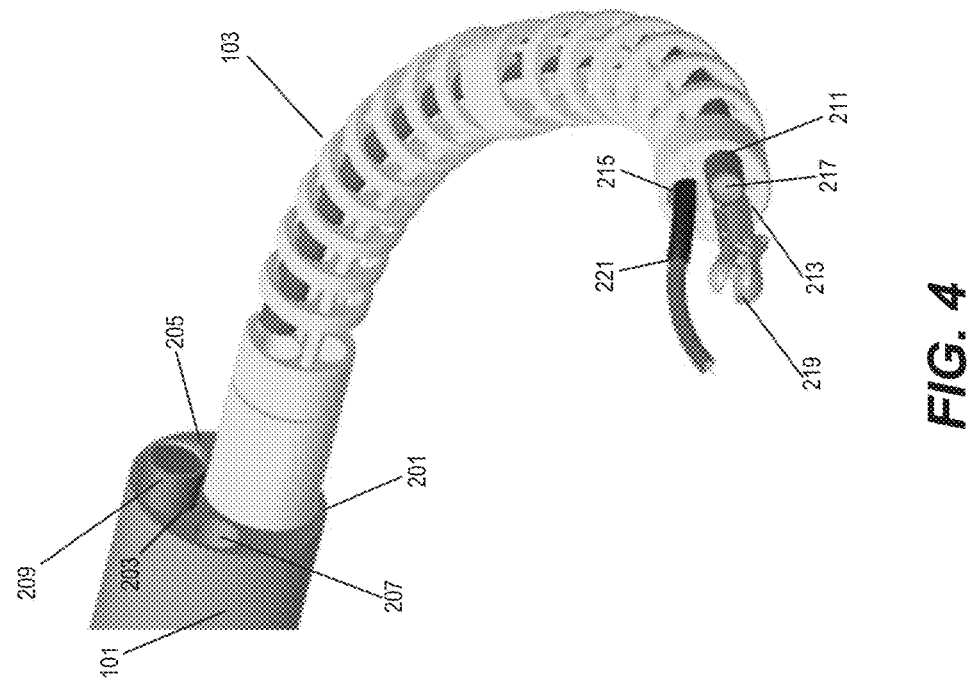
FIG. 4 is a perspective view of a dexterous arm of the robotic device of FIG. 2.

FIG. 4 illustrates the dexterous arm 103 and the distal end of the central stem 101 in further detail. The central stem 101 includes four access channels 201, 203, 205, and 207. In the illustrated example, the dexterous arm 103 is positioned within and extends from the first access channel 201. A camera system 209 is positioned within the second access channel 203 of the central stem 101. The camera system 209 in this example is not extended or retracted through the access channel 203. Instead, the camera system 209 remains stationary relative to the central stem 101 and provides images from a fixed perspective of the dexterous arm 103 and various working tools as they operate within the bladder. Alternatively, in some embodiments, a straight endoscope with an included lens is used to provide a view pointed to the side. By rotating the straight endoscope, a user can change the visible regions to provide a better view of the side walls of the bladder at a target location. FIG. 5 provides a cross-sectional view of the central stem 101 that better illustrates the location of the four access channels 201, 203, 205, and 207.

The central stem 101 in this example has a diameter of less than 9 mm is sized to fit through the same diameter of a standard resectoscope outer sheath. The first access channel 201 in this example has a diameter of 5.2 mm and the second access channel 203 has a diameter of 2.8 mm. The two other access ports 205, 207 in this example are smaller than the first and second access channels and are used for saline input and output and to maintain insufflation of the bladder.

The dexterous arm 103 includes three working channels 211, 213, and 215. In the illustrated example, a second camera system 217 is positioned within the first working channel 211, a grasper or biopsy cup 219 is positioned within the second working channel 213, and a laser ablation system 221 is positioned within the third working channel 215. While the first camera system 209 provides a fixed general view of the field, the fiberscope of the second camera system 217 provides a close view for surveillance and monitoring of fine resection. In some constructions, the fiberscope includes an integrated light. In other constructions, a separate light can be positioned in one of the three working channels of the dexterous arm 103.

Figure 6:
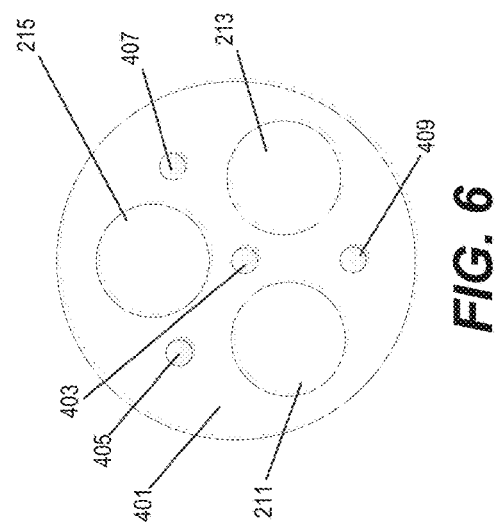
FIG. 6 is a cross-sectional view of the dexterous arm of the robotic device of FIG. 2.

The dexterous arm in this example is in the form of a continuum robot that includes multiple disks coupled together by linkages. As more clearly illustrated in FIG. 6, each disk 401 of the continuum robot includes a center hole 403. The center hole 403 is connected to a backbone shaft. Although the backbone shaft is flexible to allow the continuum robot to bend, it is fixedly connected to each disk 401 at the center hole 403 to ensure that each disk 401 remains at a fixed distance from the neighboring disks. Control fibers are extended through a series of perimeter holes 405, 407, and 409. One or more of the control fibers are controllably retracted by the second actuator system 111 to cause individual disks to tilt and to cause the continuum robot to bend as desired. Continuum robots that can be incorporated into this robotic system are known in the art as described, for example, in U.S. Patent Application Publication No. 2005/0059960 and U.S. Patent Application Publication No. 2011/0230894.

In the example of FIG. 4, the dexterous arm 103 includes two steerable snake-like segments that are each separately controllable for bending in two degrees-of-freedom. These two bending segments combined with the axial insertion degree-of-freedom provided by the push rod 109 provide a minimum of five degrees-of-freedom to locate the working tools at the distal end of the dexterous arm 103 in three-dimensions while specifying two orientation parameters with respect to the bladder wall. Furthermore, the working tools, such as the biopsy cup 219 can be extended from the working channel and rotated axially within the working channel to provide additional degrees-of-freedom.

As illustrated in FIG. 7, the laser ablation tool 221 can be aimed at a target surface by moving the position and orientation of the dexterous arm 103. In FIG. 7A, the dexterous arm positions the laser ablation tool at the center of a target area where tissue is to be removed. In FIGS. 7B and 7C, the position and orientation of the dexterous arm is moved to aim the laser ablation tool at other locations of the target tissue. FIG. 7D shows the target tissue area before laser ablation while FIG. 7E shows the target area after laser ablation is completed using the robotic device described above.

Figure 8:
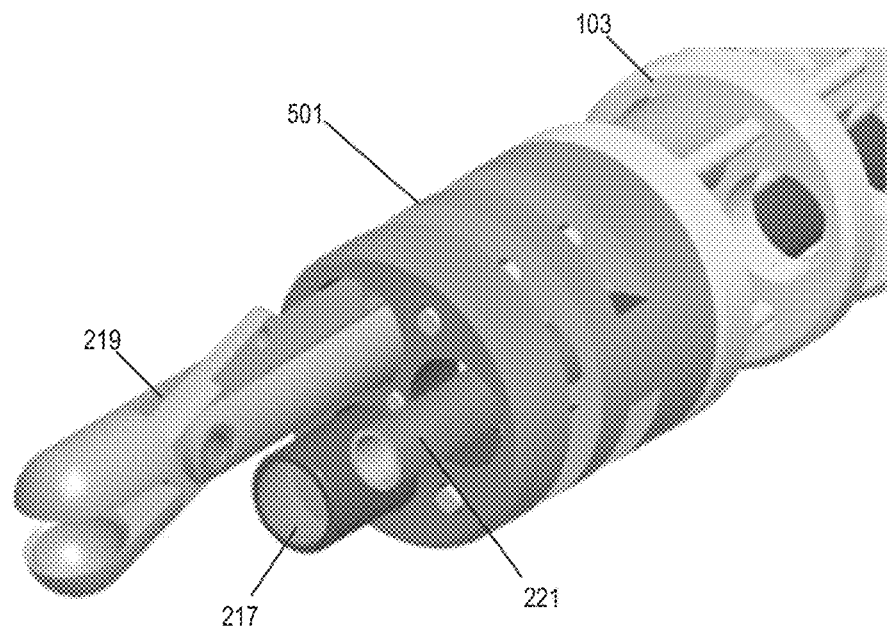
FIG. 8 is a perspective view of a tool adjustment component coupled to the distal end of the dexterous arm of the robotic device of FIG. 2.
Figure 9A:
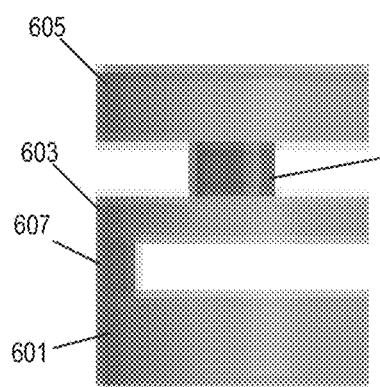
FIG. 9A is a top view of the tool adjustment component of FIG. 5.
Figure 9B:
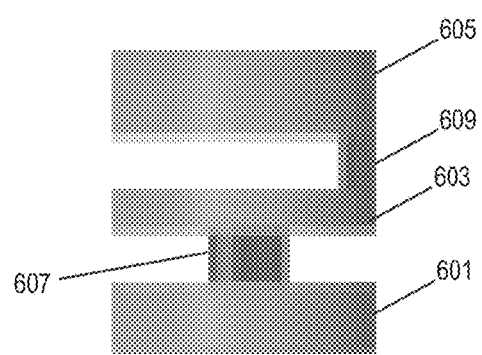
FIG. 9B is a side view of the tool adjustment component of FIG. 5.

Although the laser ablation tool 221 can be aimed at a target surface by adjusting the position and orientation of the dexterous arm, greater resection precision can be provided through independent control of the laser ablation tool 221. Independent control of the laser ablation tool 221 is achieved by a tool adjustment component 501 as illustrated in FIG. 8. The tool adjustment component 501 includes a two degree-of-freedom wrist that angulates the laser ablation fiber with respect to the distal end of the dexterous arm 103. As illustrated in FIGS. 9A and 9B, three disk segments 601, 603, and 605 are positioned concentrically and attached by flexure joints 607 and 609. The flexure joints 607 and 609 are positioned at approximately 90 degree apart along the edge of the disk segments. This configuration allows the second disk 603 to be tilted relative to the first disk 601 along a first axis while the third disk 605 is tilted relative to the second disk 603 on a second axis. Each disk is pulled/pushed by a beam passing through one of the channels in the dexterous arm 103. Because the first and second axes are substantially perpendicular, the angle of the laser ablation tool 221 can be controlled with two degrees-of-freedom.

Figure 10:
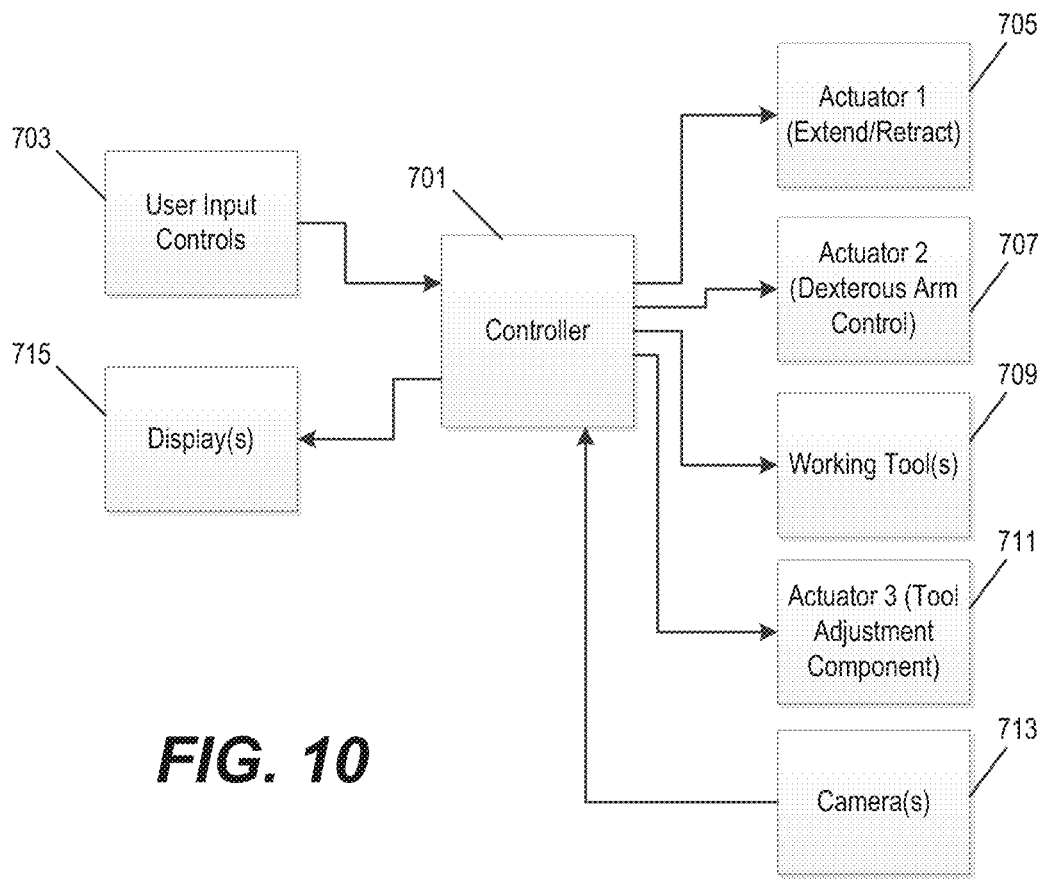
FIG. 10 is a block diagram of a control system for the robotic device of FIG. 2.

FIG. 10 illustrates a control system for the robotic device described above. A controller 701 includes a memory and a processor that executes software instructions stored on the memory. The controller 701 can be implemented as part of a stand-alone control system or integrated into a personal computer system. The controller 701 receives operational inputs from a user through a set of user input controls 703. The user input controls 703 can include, for example, one or more joystick controllers, pedals, buttons, and sliders. Based on the operational inputs, the controller 701 provides control signals to the first actuator 705 to control the extension and retraction of the dexterous arm and to the second actuator 707 to control the position and orientation of the dexterous arm. The controller 701 also provides control signals to the various working tools 709 positioned at the distal end of the dexterous arm. The controller 701 also provides control signals to an actuator 711 that controls the angle of a laser ablation tool by adjusting the tool adjustment component. The controller 701 also receives image data from both of the cameras 713 and displays the image data on a display 715.

The control system for this robotic device can be integrated within a telemanipulation system that includes a master interface (e.g., a Phantom Omni or any other haptic device with at least six degrees-of-freedom). The telemanipulation system can be implemented using the Matlab xPC Target real-time operating system with a host and a target computer. The host computer captures the mater interface input, relays the input signals to the target machine path planner, processes and displays a video stream for a steerable fiberscope and receives status and position orientation of the robot as relayed by the target computer. A surgeon using the system will have a standard fixed endoscope view and will be able to adjust the robot angle and lock it in position to that the central stem does not move relative to the patient. The surgeon also will be able to see the view from the steerable endoscope at the distal end of the dexterous arm.

The control system also provides several assistive modes to assist the surgeon in the process of surveillance and resection. In one assistive mode, virtual fixtures are defined by a user at the time of the procedure to restrict usage of working tools outside of a desired target area. In some constructions, assistive modes that define virtual fixtures operate by implementing telemanipulation control laws that define safety boundaries preventing the robot end effector (e.g., the dexterous arm and the working tools) from reaching undesired poses with the anatomy. The user manipulates the dexterous arm around the circumference of an area of interest to tag the circumference of a resection area. The user can also select one or more points inside the resection area to provide an indication of the depth of the resection area surface.

The circumference of the resection area and the depth reference points can be defined in a number of different ways. For example, the user can place the distal end of the dexterous arm in contact with the surface of the bladder and physically trace the circumference of the resection area by moving the distal end of the dexterous arm across the surface of the bladder. The dexterous arm in other constructions can be fitted with a visible laser pointing device that can be used to trace the circumference of the resection area without physically contacting the surface of the bladder.

Alternatively, the user can place the distal end of the dexterous arm in contact with the bladder surface at a point along the circumference, register the point, and then remove the distal end from the surface of the bladder before moving the distal end to another point along the circumference. The points are registered by pressing a button or a pedal to indicate to the controller that the distal end of the dexterous arm is at an appropriate place. The robot controller records the tagged points and uses them to define a "least squares" surface fit with an associated boundary curve. The boundary curve is then used to define a virtual fixture in directions locally tangential to the bladder walls and the surface fit is used to define a depth of the virtual fixture.

The controller uses variable scaling a between the user input $v_{des_m}$ and robot commanded slave velocity $v_{des_s}$ as the robot tip approaches resection depth x=a where x>a designates the bladder tissue wall interior. For example, the scaling $v_{des_s} = \alpha v_{des_m}$ where $\alpha$ is given by the equation:

$\alpha = 1$ if $x < 0$, $\alpha = \xi + (1-\xi)\beta\alpha_{min}$ if $0 \leq x \leq a$, $\alpha = \beta\alpha_{min}$ if $x > a$ where $\xi = (a-x)^n/a^n)$ (1)

Figure 11:
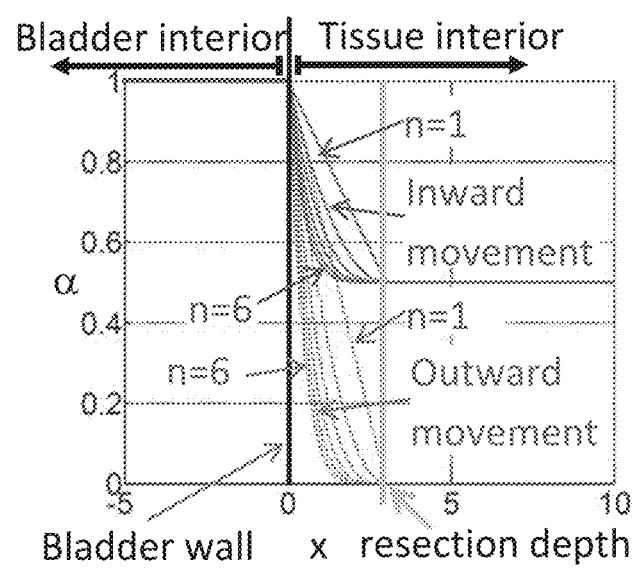
FIG. 11 is a graph illustrating scaling factors used to define a resection depth limit.

As illustrated in FIG. 11, this scaling prevents tool penetration of more than distance a into the bladder wall. In equation (1), the parameter $\beta=0$ if the user commands movement away from the bladder center. Otherwise, $\beta=1$. The scalar $\alpha_{min}$ sets a minimal scaling factor for inward speeds at the virtual fixture wall x=a. Parameter n is a power coefficient that controls how aggressive the virtual fixture is.

The master interface reflects a force to the user according to the equation:

$$f_m = -\|f_m\| v_{des_m}, \|f_m\| = f_{max}t + (1-t)f_{min}, \text{ where } t=1-\alpha \quad (1)$$

where $f_m$ is the force applied by the master on the user's hand, $f_{max}$ and $f_{min}$ are maximal and minimal resistive force magnitudes, t is a non-dimensional parameter from 0 to 1.

Once the virtual fixture has been defined, the controller restricts the operation of the working tool in areas outside of the virtual fixture. As described above, the controller receives operational inputs from the user and controls the position and operation of the dexterous arm and the working tools based on the operational inputs. However, in some constructions, the controller user will prevent the user from moving the distal end of the dexterous arm outside of the virtual fixture when the working tools are in use. Similarly, the controller can prevent the user from operating/activating the working tools when the distal end of the dexterous arm is positioned outside of the virtual fixture.

Figure 12:
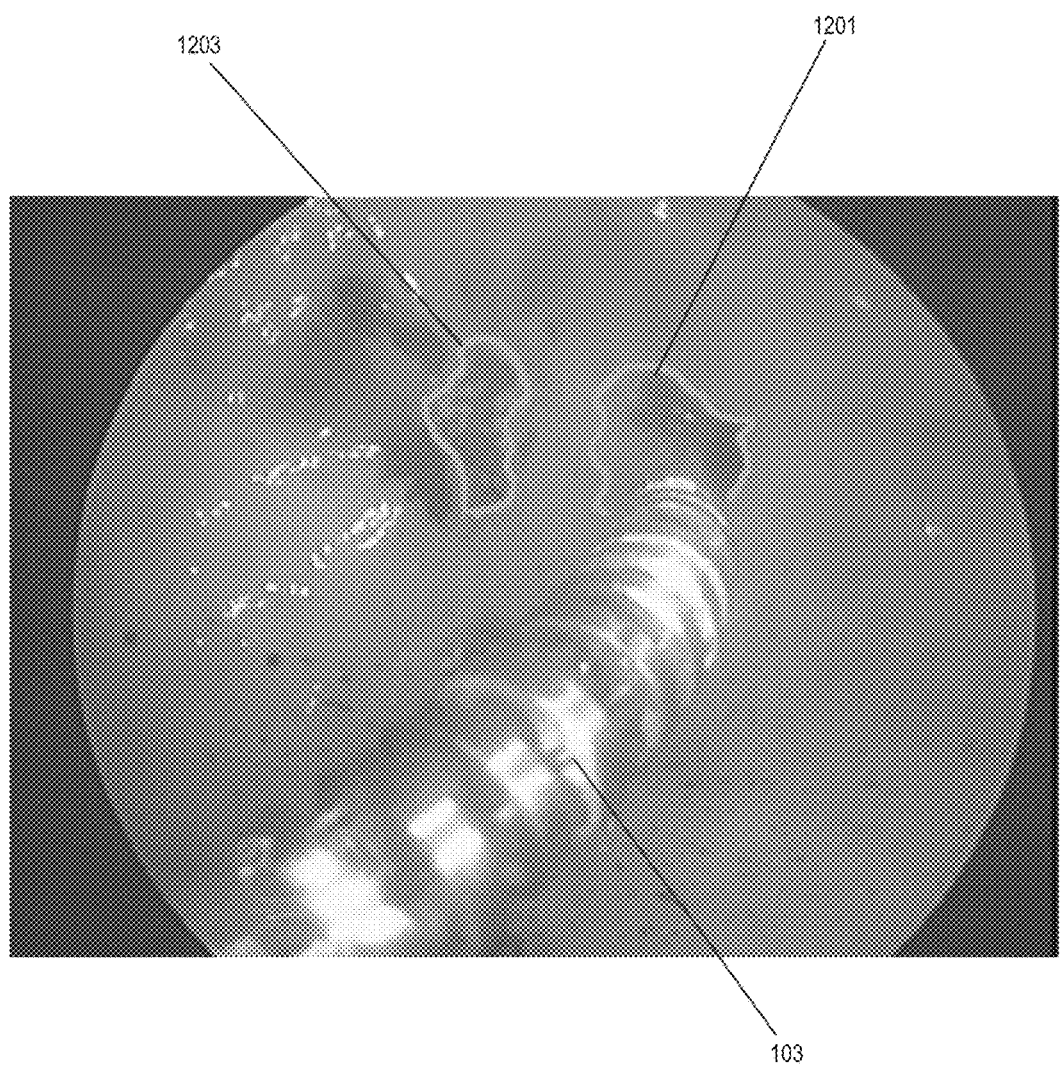
FIG. 12 is a top view of a working tool of the robotic device of FIG. 2 operating within a defined virtual fixture.

FIG. 12 shows an image captured by the camera system 209 that is mounted on the distal end of the central stem 101 (see, FIG. 2). The image shows the dexterous arm 103 positioned to allow the working tools to interact with the tissue of the bladder. Two virtual fixtures 1201 and 1203 have been defined based on tags provided by the user. In this example, the dexterous arm 103 is positioned such that the working tools can be used to perform operations within the first virtual fixture 1201. As such, the controller prevents the user from moving the dexterous arm 103 outside of the first virtual fixture while the working tools are being used. When the working tool is deactivated, the dexterous arm 103 can be moved outside of the virtual fixture 1201. However, when the dexterous arm 103 is removed from the virtual fixture 103, the operation of the working tools is restricted until the dexterous arm 103 is moved back to one of the two virtual fixtures 1201 or 1203.

The robot control interface also allows the surgeon to toggle between fully independent kinematic redundancy resolution and a micro-macro dexterity mode. In the full independent redundancy resolution, the dexterous arm and the working tools are controlled by the controller based on user input while maximizing dexterity and distance from the limits of the joints in the dexterous arm and the push rod. In the micro-macro dexterity mode, the dexterous arm is controlled by the controller using user inputs while maintaining relative positions of the tooling and resection arms fixed with respect to the distal end of the dexterous arm. Once the user has placed the distal end of the dexterous arm at a target area, he provides an input that switches the system from the full independent redundancy resolution mode to the micro-macro dexterity mode so that he can perform small movements using the working tools and the tool adjustment component of the robotic device while the dexterous arm remains stationary and provides a local close-up view of the operation site using the fiberscope/camera chip.

The controller is also configured to provide assistance to the surgeon using image data captures by the camera systems. In another assistive mode, the controller presents a three-dimensional model of the bladder in a simplified representation. The simplified representation begins as a blank sphere. The three-dimensional model is then adjusted to include image data captured by the camera systems and, in some constructions, surface characteristics based on the direct kinematics of the dexterous arm as it interacts with the bladder surface. A surgeon is able to use the interface to replay video data captured by the camera and to tag spherical coordinates that are associated with areas of interest within the bladder. The surgeon can later select one of the tagged spherical coordinates and the controller will automatically adjust the dexterous arm into a pose that visualizes the selected surgical site.

Figure 13:
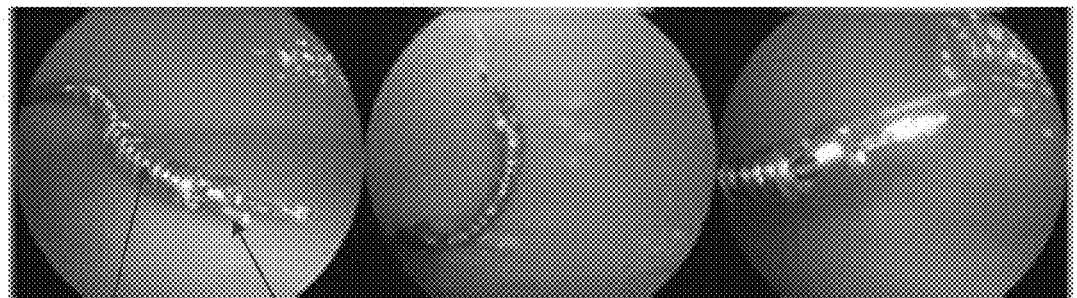
FIG. 13 is a series of three overhead views of a continuum robot being used to perform a bladder resection procedure.

Robotic systems such as those described above in reference to FIG. 1 improve and expand the repertoire of techniques of urologic surgery, to increase surgical resection accuracy, and surveillance coverage. However, in order to reach the anterior and interior quadrants of the urinary bladder (as illustrated in FIG. 13), the continuum robot 1301 needs to safely and autonomously retract inside the resectoscope allowing localized constrained telemanipulation of its end-effector 1303.

In addition to restricting movement of the end effector 1303, virtual fixture can be enforced in the configuration space of the manipulator rather than in the task space. In the case of continuum robots, the burden of safeguarding both the anatomy and the surgical slave cannot be left to the surgeon. On the other hand, intelligent surgical slaves should be able to autonomously steer away from access and anatomical constraints and adjust the inversion of the kinematics. The configuration space often provides a lower-order space in which constraints along subsequent segments can be easily and intuitively defined. The framework is evaluated on a 5 DoF continuum robot for transurethral intervention. Experimental results show the ability to cover 100% of the urinary bladder.

Figure 1:
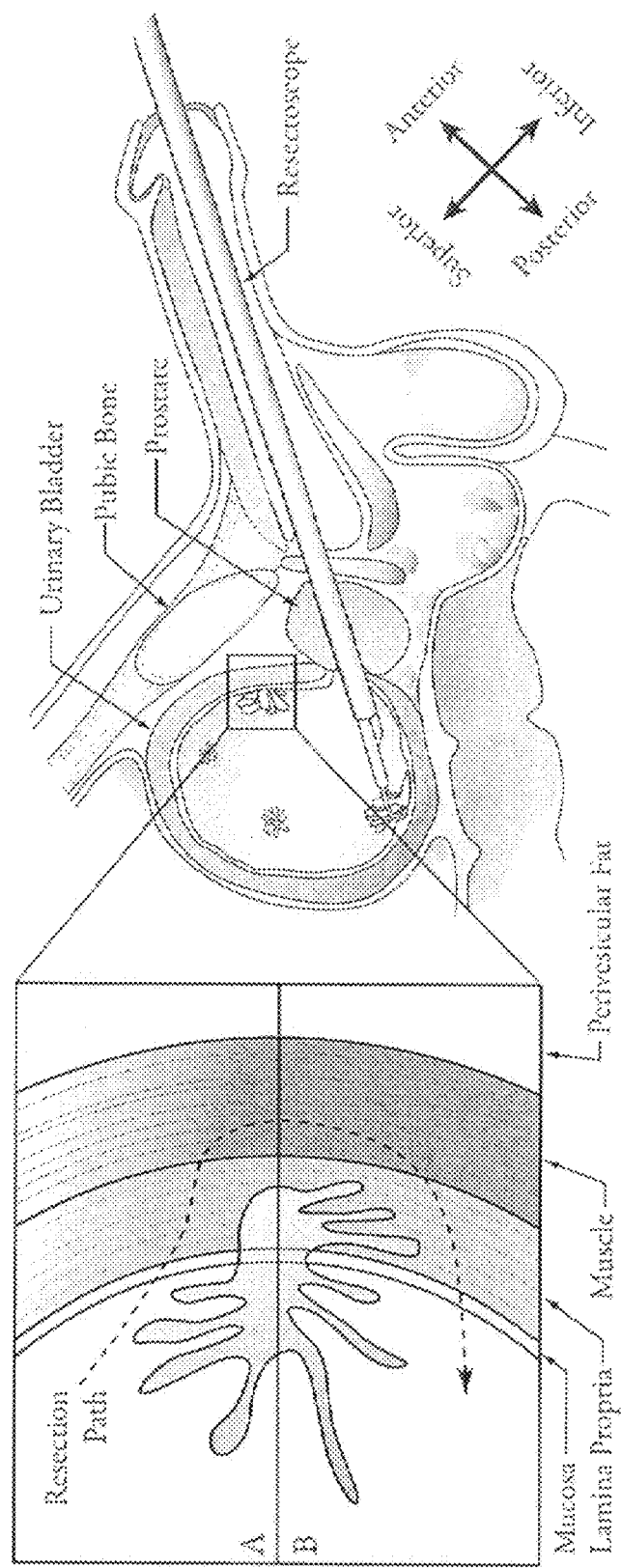
FIG. 1 is a cross-sectional view of a resectoscope inserted into a bladder transurethrally.

TURBT is an endoscopic surgical procedure that aims for resecting non-invasive tumors inside the urinary bladder. In 2012, the number of newly diagnosed bladder cancer patients and deaths in the US are expected to be 73,510 and 14,880 respectively [17]. TURBT procedures provide access to the bladder via the urologic resectoscope, a device that consists of multiple telescoping and interlocking parts. The inner diameter that is used to deliver instruments and visualization is typically between 7 and 8 mm. The resectoscope is inserted through the urethra as shown in FIG. 1.

The long straight access channel reduces dexterity at the tool tip by only allowing insertion along the resectoscope's axis and limiting lateral movements that are usually achieved by re-orienting the resectoscope and the surrounding anatomy. Coverage of the posterior and superior quadrant is difficult and accuracy of the resection highly depends on surgeon skills. Coverage of the anterior and inferior quadrant is achieved by pushing on the pubic bone in order to deform the urinary bladder internal wall.

As discussed above, these challenges are address by a telesurgical system used for deployment, laser delivery, and biopsy inside an explanted bovine bladder as illustrated in FIG. 13. Posterior and superior quadrants of the urinary bladder were easily reached and key surgical tasks were performed. On the other hand, the anterior and inferior quadrants were not easily accessed under telemanipulation control because of the inability of the operator to safely retract the continuum arm inside the resectoscope and accomplish the desired movement with the deployed portion of the manipulator.

As described in detail below, the surgical slave is adapted to actively assist the surgeon by avoiding the tubular constraint (i.e., the rigid central stem) without a priori knowledge of the task while allowing full control of the remaining DoF. Traditional virtual fixture methods that constraint the robot's end-effector may not easily exploited in this scenario because of the fact that the virtual fixtures need to be applied to section of the manipulator only (in this case the first segment). Furthermore, these virtual fixtures do not only depend on the particular access channel used but only on the insertion depth along the tubular constraint.

Figure 14:
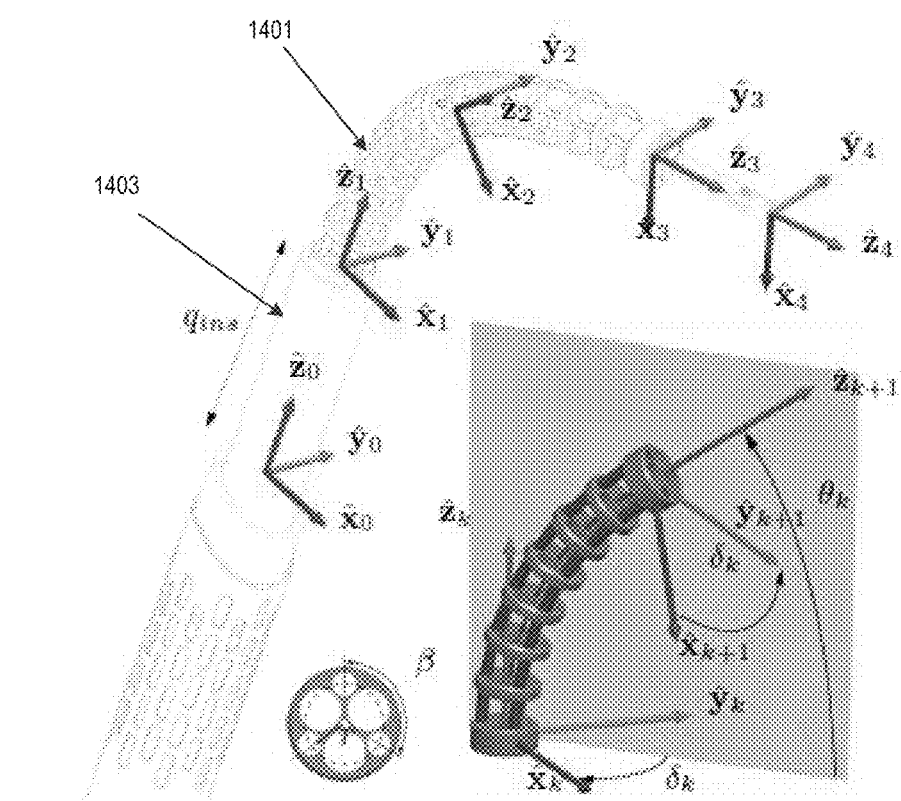
FIG. 14 is a perspective view of a continuum robot extended from resectoscope.

FIG. 14 illustrates an example of dexterous arm 1401 (i.e., a continuum robot) extended from the rigid central stem 1403). The surgical slave actuator provides a linear stage and a dexterous four DoF continuum manipulator. Each segment has three push-pull backbones that allows for bending in space. For the ease of presentation, in the remainder of this section, the kinematics of the two segments and the insertion stage is summarized.

(A) Direct Kinematics:

The direct kinematics of the surgical slave is depicted in FIG. 3. Five coordinate systems are defined: 1) base frame $\{\hat{x}_0, \hat{y}_0, \hat{z}_0\}$, 2) first segment base disk frame $\{\hat{x}_1, \hat{y}_1, \hat{z}_1\}$, 3) second segment base disk frame $\{\hat{x}_2, \hat{y}_2, \hat{z}_2\}$, 4) end effector frame $\{\hat{x}_3, \hat{y}_3, \hat{z}_3\}$, and 5) tool frame $\{\hat{x}_4, \hat{y}_4, \hat{z}_4\}$. The position and the orientation of the end-effector in base frame is given by:

$$p_3^0 = p_1^0 + R_1^0(p_2^1 + R_2^1 p_3^2)$$

$$R_3^0 = R_1^0 R_2^1 R_2^3. \quad (3)$$

where $p_1^0$ is given by the amount of insertion/retraction (see FIG. 14)

$$p_1^0 = [0 0 q_{ins}]^T, \quad (4)$$

and the position of the end disk of each segment (k=1, 2) is given by $$p_{k+1}^k = \frac{L_k}{\theta_k - \theta_0} \begin{bmatrix} \cos(\delta_k)(\sin(\theta_k) - 1) \\ -\sin(\delta_k)(\sin(\theta_k) - 1) \\ -\cos(\theta_k) \end{bmatrix} \quad k = 1, 2. \quad (5)$$

Where $L_k$ is the length of segment k, $\theta_k$ is the bending angle, $\delta_k$ defines the angle in which segment k bends, $q_{ins}$ is the displacement of frame $\{1\}$ from frame $\{0\}$ along $\hat{z}_0$, $\theta_0 = \pi/2$, $R_1^0$ is the identify matrix (see [2] for a design in which the first segment base disk rotates), $$R_{k+1}^k = Rot(-\delta_k, \hat{z}) Rot(\theta_0 - \theta_k, \hat{y}) Rot(\delta_k, \hat{z}) \quad (6)$$

and operator Rot($\varphi$, $\hat{w}$) returns a rotation of angle $\varphi$ about axis $\hat{w}$. The direct kinematics of the surgical slave is easily updated if a tool is deployed through one of its access channels. In this case, the position of the tools is given by:

$$p_4^0 = p_3^0 + R_3^0 [\tau_c \cos \beta \tau_c \sin \beta d_3]^T \quad (7)$$

We now define the configuration space $\Psi \in \mathbb{R}^5$ and the joint space $q \in \mathbb{R}$. The configuration space is defined as:

$$\Psi = [\theta_1 \delta_1 \theta_2 \delta_2 q_{ins}]^T \quad (8)$$

where the joint space is defined as:

$$q = [q1,1 q1,2 q1,3 q2,1 q2,2 q2,3 q_{ins}]^T \quad (9)$$

where, for segments k=1, 2 and backbones i=1, 2, 3:

$$q_{k,i} = r \cos(\delta_k + i\beta)(\theta_i - \theta_0). \quad (10)$$

(B) Differential Kinematics:

The end-effector translational and rotational velocities are obtained as:

$$v_{0,3}^0 = v_{0,1}^0 + R_1^0(v_{1,2}^1 + R_2^1 v_{2,3}^2 + \omega_{1,2}^1 \times R_2^1 p_3^2) \quad (11)$$

$$\omega_{0,3}^0 = R_1^0 \omega_{1,2}^1 + R_2^0 \omega_{2,3}^2 \quad (12)$$

where $v_{a,b}^c$ and $\omega_{a,b}^c$ are the translational and rotational velocities of frame b with respect to frame a written in frame c. The translational velocity of frame $\{1\}$, $v_{0,1}^0$, is given by differentiating (3) with respect to time while the translational velocities of the first, $v_{1,2}{}^1$, and second end disk, $v_{2,3}{}^2$, in local coordinate frames is given by differentiating (4) with respect to time for k=1, 2.

Rotational velocity $\omega_{1,2}{}^1$ and $\omega_{2,3}{}^2$ are given by (for k=1, 2):

$$\omega_{k-1,k}{}^{k-1} = \dot{\theta}_k \hat{y}_k^{k-1} + \dot{\delta}_k(\hat{z}_k^{k-1} - \hat{z}_{k-1}^{k-1}). \tag{13}$$

By defining $\dot{\Psi}$ as the rate of change of the configuration space vector $\Psi$, one can rewrite the twist of the end-effector (i.e. Equations (12) and (13)) as:

$$\begin{bmatrix} v_{0,3}^0 \\ \omega_{0,3}^0 \end{bmatrix} = J_{arm}\dot{\Psi}. \tag{14}$$

where $e_3=[0\ 0\ 1\ 0\ 0\ 0]^T$. Assuming circular bending, each continuum segment Jacobian k=1, 2 is then given by:

$$J_k = \begin{bmatrix} L_k c_{\delta_k} \frac{\Theta_k c_{\theta_k} - s_{\theta_k} + 1}{\Theta_k^2} & -\frac{L_k s_{\theta_k}(s_{\theta_k} - 1)}{\Theta_k} \\ -L_k s_{\delta_k} \frac{\Theta_k c_{\theta_k} - s_{\theta_k} + 1}{\Theta_k^2} & -\frac{L_k c_{\theta_k}(s_{\theta_k} - 1)}{\Theta_k} \\ L_k \frac{\Theta_k s_{\theta_k} + c_{\theta_k}}{\Theta_k^2} & 0 \\ -s_{\delta_k} & c_{\delta_k} c_{\theta_k} \\ -c_{\delta_k} & -s_{\delta_k} c_{\theta_k} \\ 0 & -1 + s_{\theta_k} \end{bmatrix} \tag{15}$$

Where $c_y=\cos(y)$, $s_y=\sin(y)$, and transformation matrices $S_1$ and $S_2$ are given by:

$$S_1 = \begin{bmatrix} I & [-{}^0R_2{}^2p_3]\times \\ 0 & I \end{bmatrix} \tag{16}$$

$$S_2 = \begin{bmatrix} {}^0R_2 & 0 \\ 0 & {}^0R_2 \end{bmatrix}.$$

C. Constrained Redundancy Resolution:

The surgical slave is teleoperated using a Sensable Phantom Omni and the master/slave trajectory planner. Once the desired twist of the slave's end-effector, $t_{des}$, is obtained, the constrained configuration space velocities, $\dot{\Psi}_{des}$, that approximate the desired motion are computed. The surgical slave is only capable to control 3 translational DoFs and two rotational DoFs (point in space). Furthermore, when the first segment is retracted inside the tubular constraint, the controllable DoFs drops to 3 (2 rotational DoFs and insertion along the resectoscope). For these reasons, we defined a primary task and secondary task. The primary task consists of controlling the two rotational DoFs (rotations about $\hat{x}_0$ and $\hat{y}_0$) and one translational DoF (along $\hat{z}_0$) while the secondary task consists of controlling the remaining two translational DoF (along $\hat{x}_0$ and $\hat{y}_0$).

Designating tee and Jee as the end effector twist and Jacobian in end-effector frame, one may describe the primary and secondary tasks by:

$$J_{S_p}\dot{\Psi}_{des} = S_p t_{ee}, J_{S_s}\dot{\Psi}_{des} = S_s t_{ee} \tag{17}$$

where $J_{S_p}$ and $J_{S_s}$ are defined by selecting the corresponding task-specific rows of the Jacobian:

$$J_{S_p} = S_p J_{ee}, J_{S_s} = S_s J_{ee} \tag{18}$$

and selection matrices $S_p$ and $S_s$ are given by:

$$S_p = \begin{bmatrix} 0 & 0 & 1 & 0 & 0 \\ 0 & 0 & 0 & 1 & 0 \\ 0 & 0 & 0 & 0 & 1 \end{bmatrix}, \tag{19}$$

$$S_s = \begin{bmatrix} 1 & 0 & 0 & 0 & 0 \\ 0 & 1 & 0 & 0 & 0 \end{bmatrix}$$

The end effector twist and Jacobian are given by:

$$J_{ee} = [\ I_{5\times 5}\ \ 0_{5\times 1}\ ] \begin{bmatrix} R_3^{0T} & 0_{3\times 3} \\ 0_{3\times 3} & R_3^0{}^T \end{bmatrix} J_{arm} \tag{20}$$

$$t_{ee} = [\ I_{5\times 5}\ \ 0_{5\times 1}\ ] \begin{bmatrix} R_3^{0T} & 0_{3\times 3} \\ 0_{3\times 3} & R_3^{0T} \end{bmatrix} t_{des}. \tag{21}$$

The desired configuration space velocity is therefore given by:

$$\dot{\Psi}_{des} = (J_{S_p}{}^\dagger S_p + (I - J_{S_p}{}^\dagger J_{S_p}) J_{S_s}{}^\dagger S_s) t_{ee} \tag{22}$$

and superscript † indicates pseudo-inverse. Equation (22) partitions the commanded twist, $t_{ee}$, into a primary task (defined by selection matrix $S_p$) and a secondary task (defined by selection matrix $S_s$). Equations (20) and (21) are respectively the Jacobian matrix and the end-effector twist expressed in end-effector frame without the angular velocity component about axis $\hat{z}_3$. By doing so, any commanded twist about that axis is ignored by the redundancy resolution and the continuum manipulator is controlled in 5 DoF.

D. Virtual Fixture Design and Implementation:

We now define two orthogonal spaces that partition the configuration space into a subspace of forbidden velocities $\{\overline{V}\}$ and a space of allowed velocities $\{V\}$. We can therefore two projection matrices that project the configuration space velocities of Equation (22) into forbidden and allowed velocities:

$$\overline{P} = \overline{V}(\overline{V}^T\overline{V})^\dagger\overline{V}^T \tag{23}$$

$$P = I - \overline{P} \tag{24}$$

where † denotes pseudo-inverse for the case where $\overline{V}$ is (column) rank deficient. For example, in the case of a tubular constraint, as the first segment of the continuum manipulator retracts inside the resectoscope, negative $\dot{\theta}_1$ is the forbidden configuration velocity and $\overline{V}$ is defined as $$\overline{V} = [1\ 0\ 0\ 0\ 0]^T. \tag{25}$$

The desired configuration space velocity is therefore given by:

$$\dot{\Psi}_{des} = P\dot{\Psi}_{des} + k_d \overline{P} u \tag{26}$$

where $u=f(\Psi)$ is a signed configuration space distance of the actual configuration $\Psi_{curr}$ to the one imposed by the virtual fixture $\Psi_{fix}$, and scalar kd determines how quickly the continuum manipulator is moved to the desired configuration. In the case of the surgical slave of FIG. 14, vector u and projection matrices $\overline{P}$, P depend on the insertion variable q along the resectoscope.

The desired configurations vector $\Psi_{des}$ is then obtained via Resolved Motion Rate:

$$\Psi_{des} = \Psi_{curr} + \Delta_t \dot{\Psi}_{des} \quad (27)$$

Once the desired configuration vector is obtained, using the kinematics relationship, one can compute the desired joint space position to be fed to the actuation compensation subsystem.

The application of virtual fixtures in the configuration space of the robot rather than in the operational space allows for easy correction of the motion of any portion of the continuum manipulator. The computation of projection matrices $\overline{P}$, $P$ and vector $u$ is shown in Algorithm 1. As the robot is commanded to retract inside the resectoscope, the $\dot{\theta}_1$ direction is defined as forbidden and $u$ depends on the following safe bending angle:

$$\theta_{1,safe} = \theta_{min} + (\theta_0 - \theta_{min})\frac{\|q_{ins}\|}{L_1}. \quad (28)$$

Figure 15:
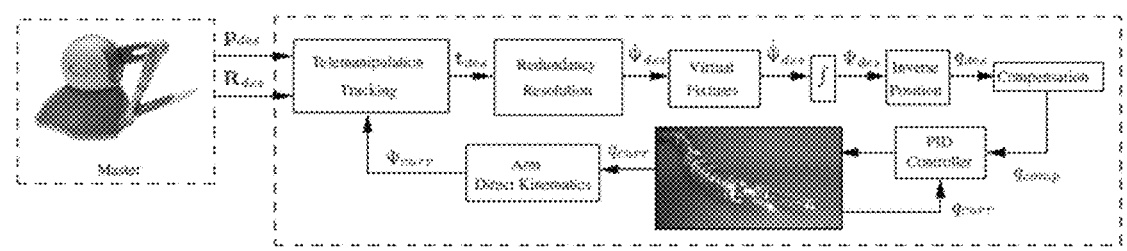
FIG. 15 is a functional block diagram of a control system for controlling the positioning and movement of the continuum robot.

FIG. 15 shows the complete control architecture of the surgical continuum robot. The desired pose is obtained from the master manipulator (Phantom Omni) at 125 Hz over the local area network. The telemanipulation tracking subsystem generates the desired task-space velocities according to the master-slave map. The redundancy resolution is implemented while the virtual fixtures subsystems constructs and enforces the configuration space virtual fixtures as described below according to the algorithm of FIG. 16. Once the desired configuration space velocities are obtained, the desired joint-space positions are computed via the close-form inverse position analysis of the continuum manipulator and a model-based actuation compensation scheme.

Thus, the invention provides, among other things, a robotic device for performing transurethral surveillance and other procedures within the bladder of a patient. A controller is configured to provide assistive mechanisms to prevent the robotic device from causing damage outside of a target resection area and can also allow for automatic placement of a working tool at a tagged location. Various features and advantages of the invention are set forth in the following claims.

What is claimed is:

1. A robotic system for procedures in a cavity, the robotic system comprising:
   a rigid central stem including an access channel positioned longitudinally along the rigid central stem;
   a dexterous arm at least partially positioned within the access channel of the central stem, the dexterous arm including a plurality of individually adjustable segments; and
   a control system including an electronic processor and configured to adjust a position of the dexterous arm by
      receiving a positioning command from a manipulator control indicative of a desired movement of a distal end of the dexterous arm,
      defining a virtual fixture representative of interior surface dimensions of the access channel of the rigid central stem, and
      controllably adjusting one or more individually adjustable segments of the plurality of individually adjustable segments based on the received positioning command such that the distal end of the dexterous arm extended beyond the distal end of the access channel performs the desired movement while lateral movements of a portion of the dexterous arm positioned within the access channel are controllably limited by the control system based on the defined virtual fixture.

2. The robotic system of claim 1 further comprising a working tool positioned at the distal end of the dexterous arm, and wherein the working tool includes at least one of a grasper and a laser ablation system.

3. The robotic system of claim 1, wherein the virtual fixture representative of the access channel of the rigid central stem is defined based on a relative linear position of the dexterous arm within the access channel and a known geometry of the access channel.

4. The robotic system of claim 3, further comprising an actuator configured to control the relative linear position of the dexterous arm within the access channel by advancing and retracting the dexterous arm.

5. The robotic system of claim 4, wherein the distal end of the dexterous arm does not extend beyond the distal end of the central stem when the dexterous arm is fully retracted by the actuator system.

6. The robotic system of claim 5, wherein the control system is configured to restrict lateral movement of all segments of the dexterous arm to within the defined virtual fixture representative of the rigid central stem when the dexterous arm is fully retracted.

7. The robotic system of claim 5, wherein the control system is configured to restrict lateral movement of the distal end of the dexterous arm to within the defined virtual fixture and prevents the distal end from performing the desired movement when the dexterous arm is fully retracted.

8. The robotic system of claim 1, further comprising:
   an actuator coupled to the dexterous arm at a proximal end of the rigid central stem; and
   a plurality of control fibers each coupled between the actuator and a different one of the plurality of individually adjustable segments, wherein the actuator is configured to selectively control linear movement of each individual control fiber of the plurality of control fibers,
   wherein the control system is configured to adjust the one or more individually adjustable segments of the plurality of individually adjustable segments by causing the actuator to apply a first linear force to a first control fiber to cause a tilting of a first segment of the plurality of segments, and
   wherein the control system is configured to controllably limit lateral movement of the individually adjustable segments by causing the actuator to apply a second linear force to a second control fiber to counteract a tilting force applied to second segment of the plurality of segments by bending of other segments of the dexterous arm.

9. The robotic system of claim 1, wherein the control system is further configured to adjust the position of the dexterous arm by
   applying a primary adjustment task in response to receiving the positioning command; and
   applying a secondary adjustment task after performing the primary adjustment task,
   wherein applying the primary adjustment task includes advancing a position of the dexterous arm and adjusting a rotational position of the dexterous arm based on the received positioning command, and
   wherein applying the second adjustment task includes adjusting and controllably limiting movement of the individually adjustable segments to cause a controlled bending of the dexterous arm based on the received positioning command.

10. A robotic system for procedures in a cavity, the robotic system comprising:
- a rigid central stem including an access channel positioned longitudinally along the rigid central stem;
- a dexterous arm extendibly positioned within the access channel of the central stem, the dexterous arm including a plurality of adjustable segments and an end effector at a distal end of the dexterous arm; and
- a control system configured to adjust a position of the dexterous arm by
  - determining a set of configuration space velocities indicative of a desired movement for the end effector of the dexterous arm, wherein the set of configuration space velocities includes a velocity for adjusting a bend angle for each segment of the plurality of adjustable segments;
  - determining a set of forbidden velocities, wherein the set of forbidden velocities identifies any segments of the plurality of adjustable segments that is retracted inside the access channel;
  - calculating a set of constrained configuration space velocities, wherein the set of constrained configuration space velocities approximates the desired movement of the end effector without adjusting the bend angle of any segment identified by the forbidden velocities; and
  - adjusting the position of the dexterous arm by adjusting a bend angle of one or more segments of the plurality of adjustable segments based on the set of constrained configuration space velocities.

* * * * *

UNITED STATES PATENT AND TRADEMARK OFFICE
CERTIFICATE OF CORRECTION

PATENT NO. : 9,956,042 B2
APPLICATION NO. : 14/271345
DATED : May 1, 2018
INVENTOR(S) : Nabil Simaan et al.

Page 1 of 1

It is certified that error appears in the above-identified patent and that said Letters Patent is hereby corrected as shown below:

On the Title Page

Item (72), please correct fourth inventor name:
"Stanley Duke Herrel" to --Stanley Duke Herrell--

Signed and Sealed this
Twenty-third Day of June, 2020

Andrei Iancu
*Director of the United States Patent and Trademark Office*